(12) United States Patent
Uchida et al.

(10) Patent No.: US 10,488,634 B2
(45) Date of Patent: Nov. 26, 2019

(54) IMAGE PICKUP APPARATUS AND OPTICAL APPARATUS USING THE SAME

(71) Applicant: OLYMPUS CORPORATION, Hachioji-shi, Tokyo (JP)

(72) Inventors: Yoshihiro Uchida, Hachioji (JP); Keisuke Takada, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 55 days.

(21) Appl. No.: 15/946,377

(22) Filed: Apr. 5, 2018

(65) Prior Publication Data
US 2018/0224638 A1    Aug. 9, 2018

Related U.S. Application Data

(63) Continuation of application No. PCT/JP2015/078897, filed on Oct. 13, 2015.

(51) Int. Cl.
*G02B 9/12* (2006.01)
*G02B 13/04* (2006.01)
(Continued)

(52) U.S. Cl.
CPC .......... *G02B 13/04* (2013.01); *A61B 1/00096* (2013.01); *A61B 1/041* (2013.01);
(Continued)

(58) Field of Classification Search
CPC .... G02B 13/04; G02B 13/0035; G02B 13/18; G02B 23/243; G02B 9/12; A61B 1/00096; A61B 1/041; B60Y 2400/3015
(Continued)

(56) References Cited

U.S. PATENT DOCUMENTS

| 5,418,649 A | 5/1995 | Igarashi |
| 2004/0160682 A1 | 8/2004 | Miyano |

(Continued)

FOREIGN PATENT DOCUMENTS

| JP | 02208617 A | 8/1990 |
| JP | 05307139 A | 11/1993 |

(Continued)

OTHER PUBLICATIONS

International Search Report (ISR) dated Dec. 8, 2015 issued in International Application No. PCT/JP2015/078897.
(Continued)

*Primary Examiner* — William Choi
(74) *Attorney, Agent, or Firm* — Holtz, Holtz & Volek PC

(57) ABSTRACT

An image pickup apparatus includes an optical system which includes a plurality of lenses, and an image sensor which is disposed at an image position of the optical system, wherein the optical system includes in order from an object side, a first lens having a negative refractive power, an aperture stop, a second lens having a positive refractive power, and a third lens having a positive refractive power, and each of the first lens, the second lens, and the third lens is formed of a material having a refractive index not higher than 1.70, and the following conditional expressions (1), (2), (3), and (4) are satisfied:

$$0 < f3/f2 \leq 1.7 \quad (1),$$
$$0.5 < \Phi 1L/IH < 3.0 \quad (2),$$
$$0.05 < D1R2L/\Sigma d < 0.5 \quad (3), \text{ and}$$
$$-0.4 < f1/R1L < 0.2 \quad (4).$$

13 Claims, 23 Drawing Sheets

(51) Int. Cl.
*G02B 13/18* (2006.01)
*A61B 1/04* (2006.01)
*G02B 13/00* (2006.01)
*A61B 1/00* (2006.01)
*G02B 23/24* (2006.01)

(52) U.S. Cl.
CPC ......... *G02B 13/0035* (2013.01); *G02B 13/18* (2013.01); *G02B 23/243* (2013.01); *B60Y 2400/3015* (2013.01); *G02B 9/12* (2013.01)

(58) Field of Classification Search
USPC ........................................ 359/716, 753, 784
See application file for complete search history.

(56) References Cited

U.S. PATENT DOCUMENTS

| | | |
|---|---|---|
| 2007/0014033 A1 | 1/2007 | Shinohara |
| 2009/0141364 A1 | 6/2009 | Baba |
| 2011/0249349 A1 | 10/2011 | Asami |
| 2011/0286112 A1 | 11/2011 | Orihara et al. |
| 2012/0016199 A1 | 1/2012 | Baba et al. |
| 2016/0223796 A1* | 8/2016 | Lee .......................... G02B 9/62 |

FOREIGN PATENT DOCUMENTS

| | | |
|---|---|---|
| JP | 2007011237 A | 1/2007 |
| JP | 2009136387 A | 6/2009 |
| JP | 4406299 B2 | 1/2010 |
| JP | 2010107815 A | 5/2010 |
| JP | 2010246906 A | 11/2010 |
| JP | 2011237750 A | 11/2011 |
| JP | 4843121 B2 | 12/2011 |
| WO | 2011027622 A1 | 3/2011 |

OTHER PUBLICATIONS

Written Opinion dated Dec. 8, 2015 issued in International Application No. PCT/JP2015/078897.
Japanese Office Action (and English language translation thereof) dated Jun. 13, 2019 issued in counterpart Japanese Application No. 2017-545018.
International Preliminary Report on Patentability (IPRP) (and English language translation thereof) dated Apr. 26, 2018 issued in counterpart International Application No. PCT/JP2015/078897.

* cited by examiner

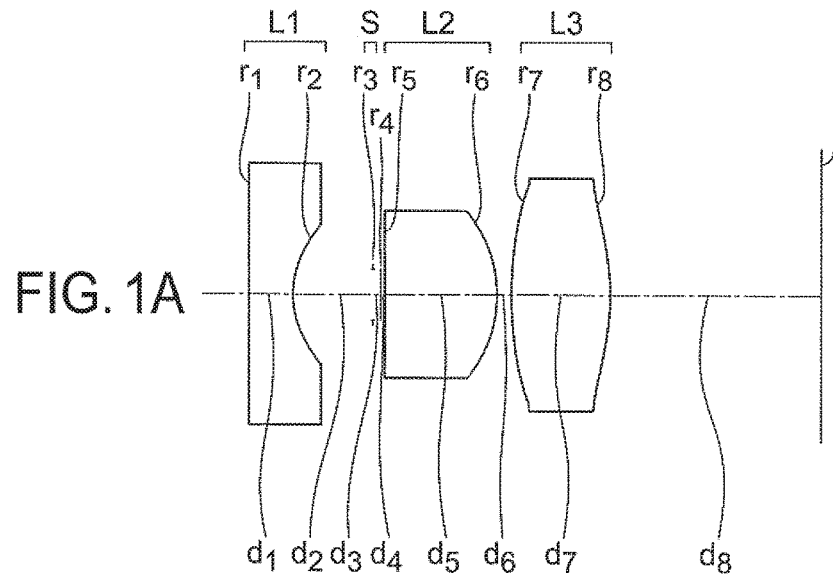
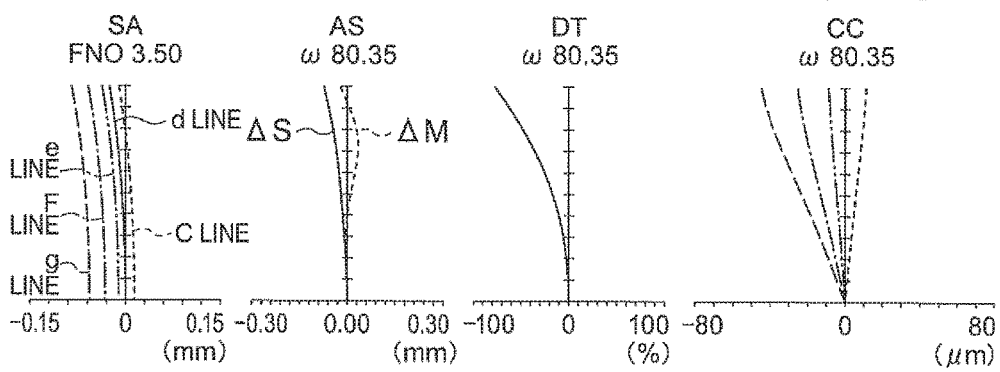

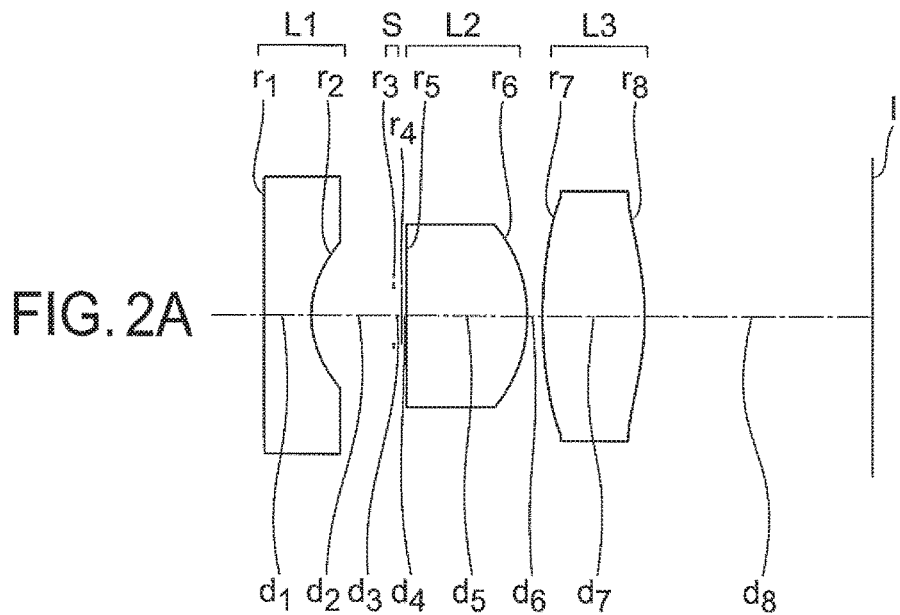
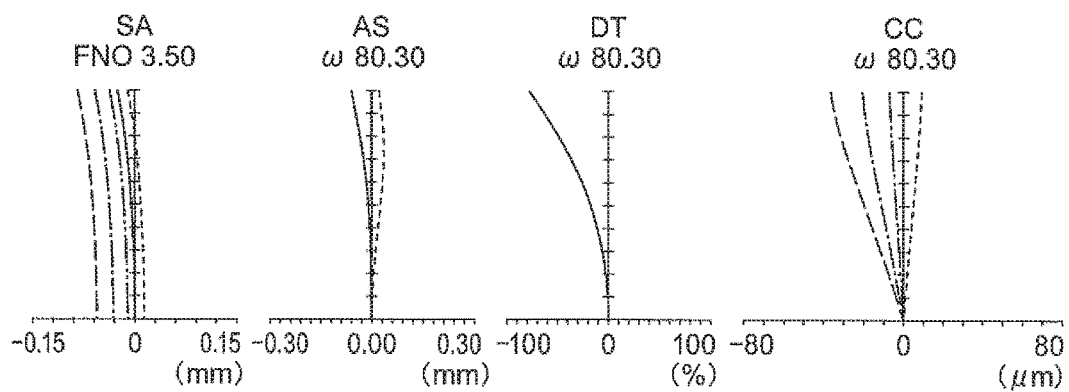

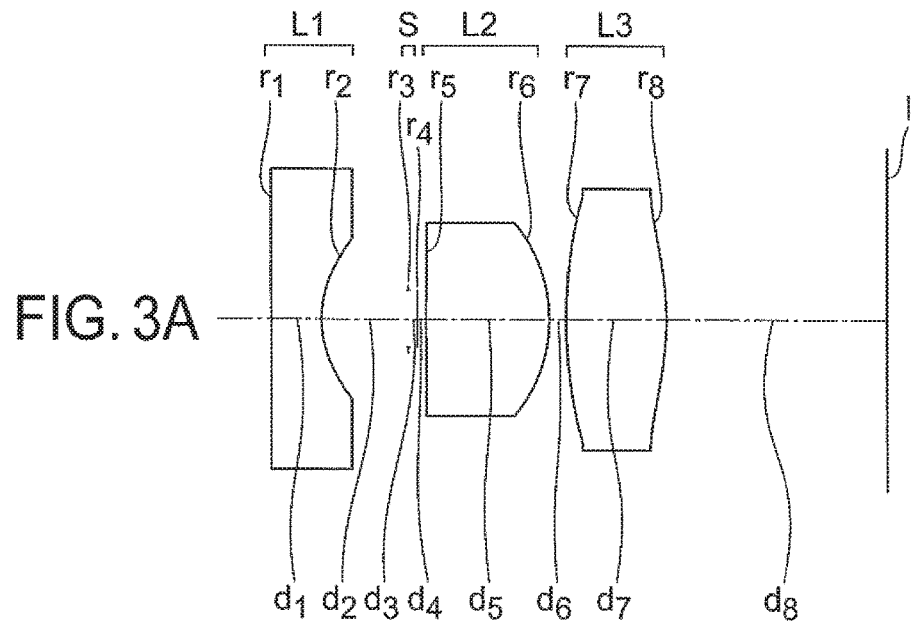
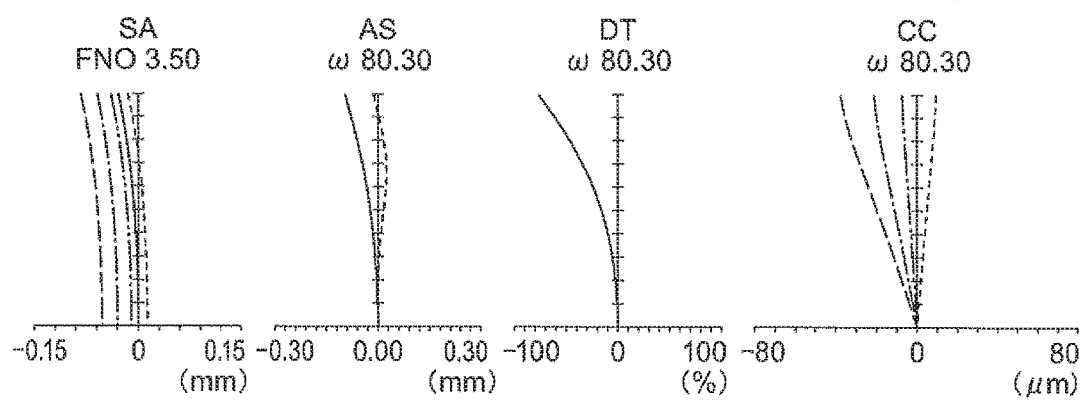

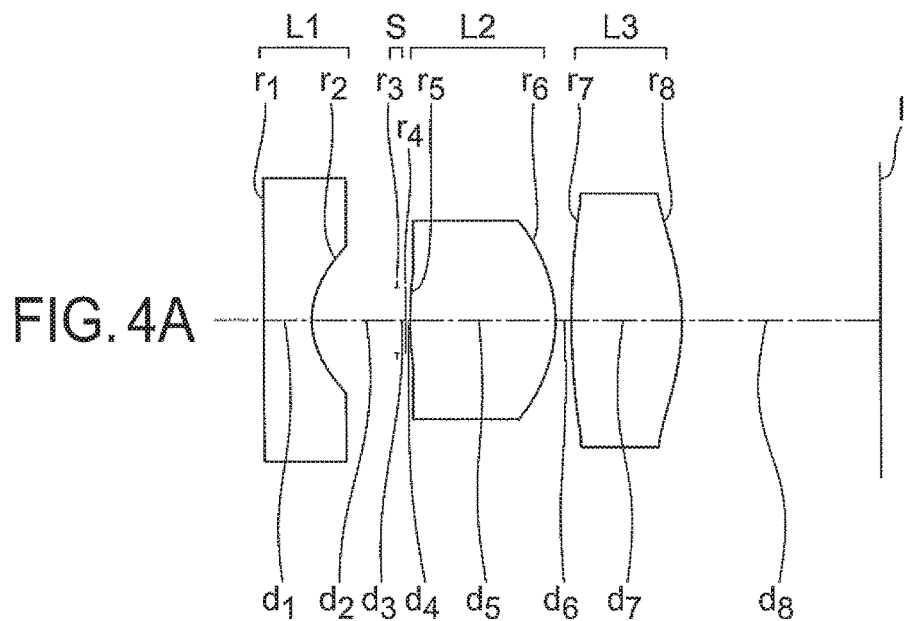
FIG. 4A
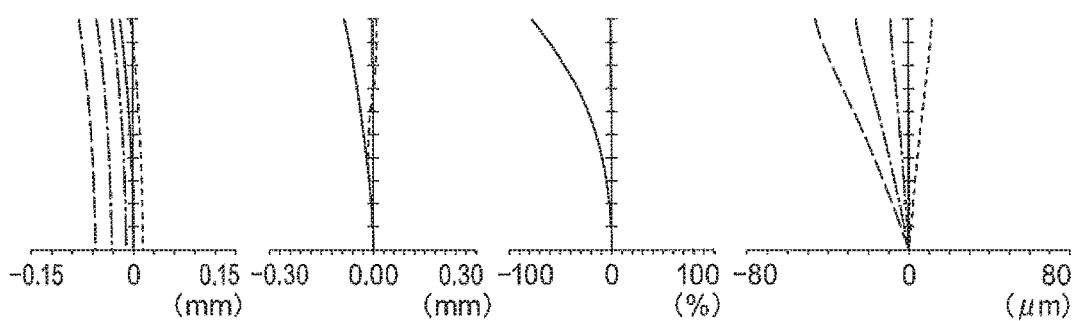
FIG. 4B
SA
FNO 2.80
FIG. 4C
AS
ω 80.30
FIG. 4D
DT
ω 80.30
FIG. 4E
CC
ω 80.30

SA
FNO 2.80

AS
ω 80.30

DT
ω 80.30

CC
ω 80.30

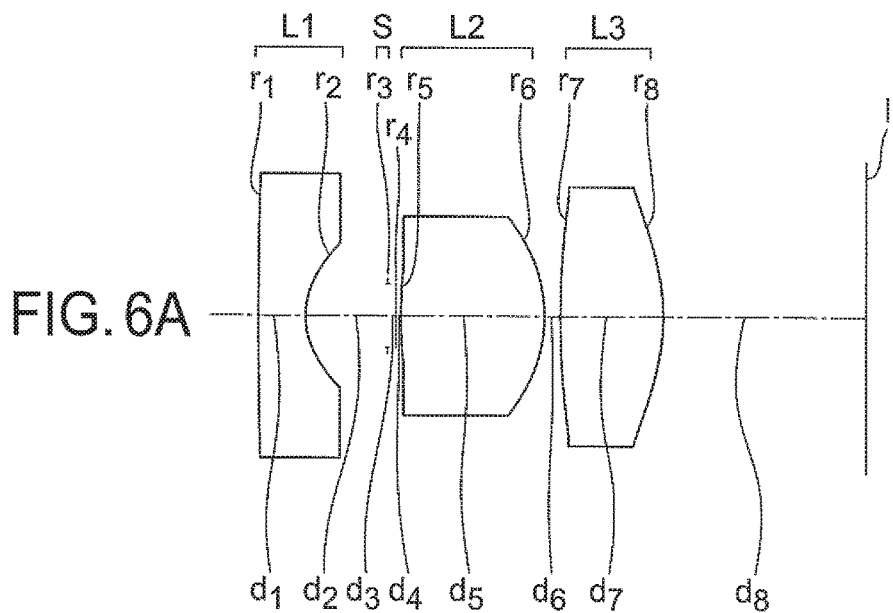
FIG. 6A
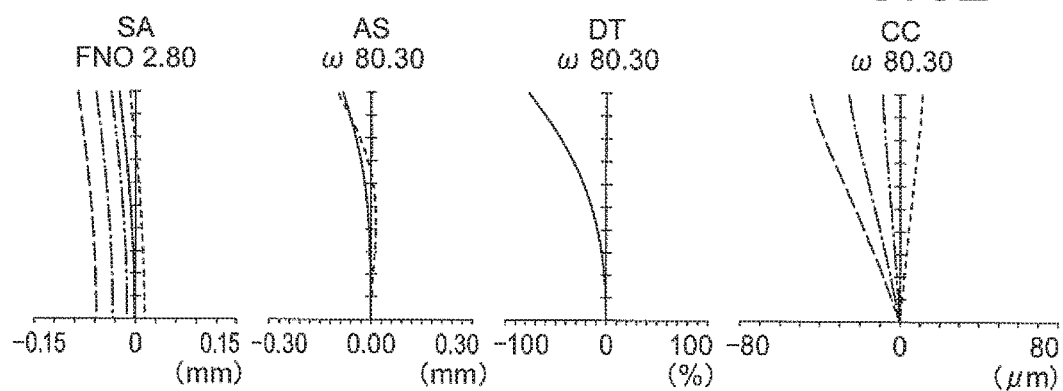
FIG. 6B
SA
FNO 2.80
FIG. 6C
AS
ω 80.30
FIG. 6D
DT
ω 80.30
FIG. 6E
CC
ω 80.30

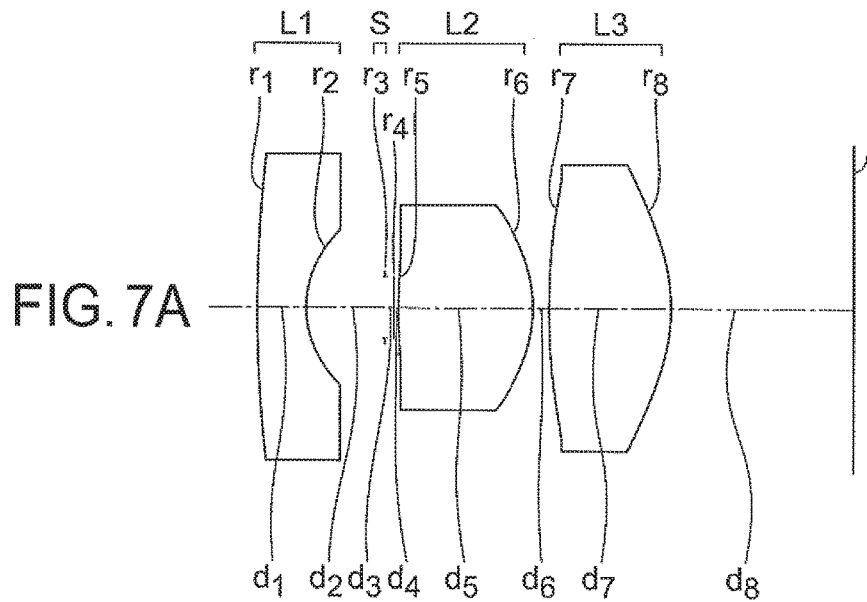
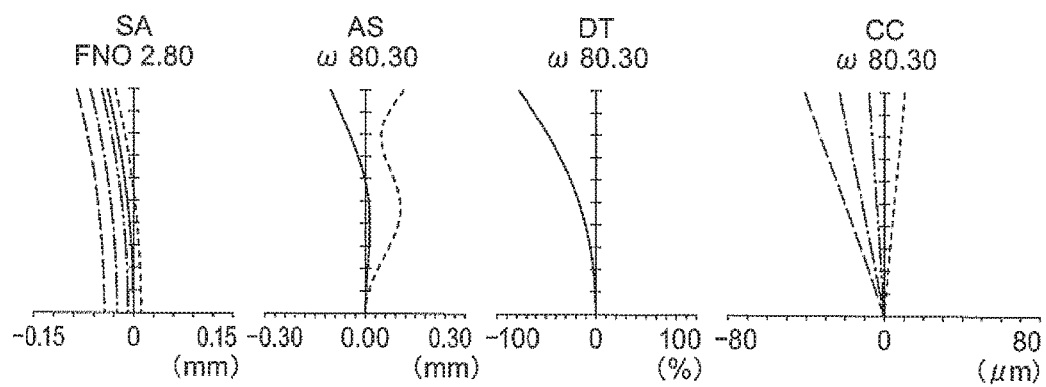

SA      AS       DT       CC
FNO 2.80  ω 75.30  ω 75.30  ω 75.30

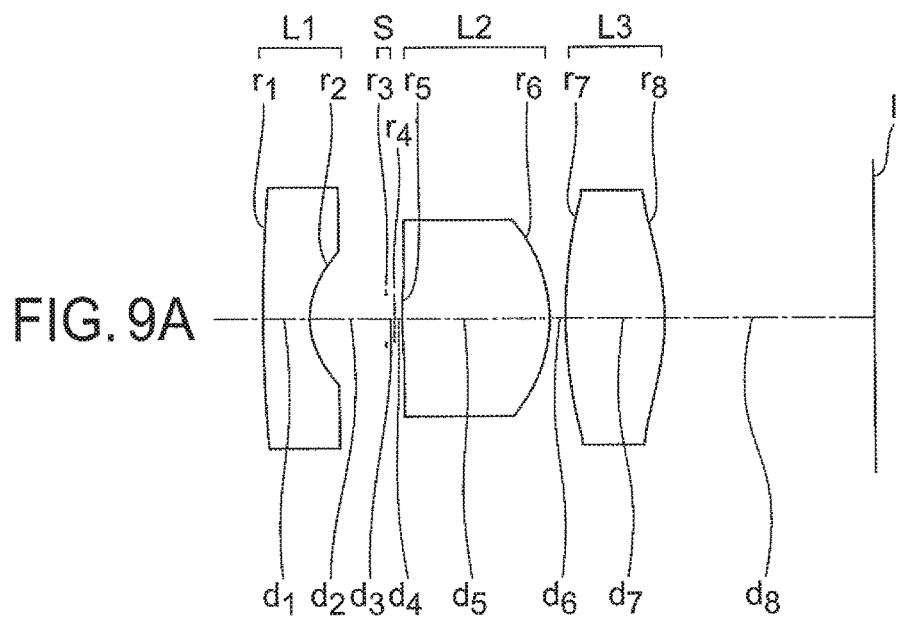
FIG. 9A
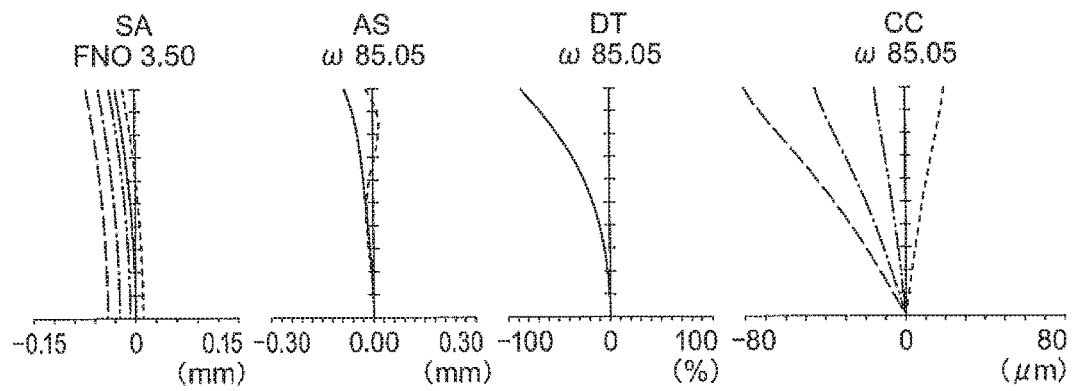
FIG. 9B
SA
FNO 3.50
-0.15  0  0.15
(mm)
FIG. 9C
AS
ω 85.05
-0.30  0.00  0.30
(mm)
FIG. 9D
DT
ω 85.05
-100  0  100
(%)
FIG. 9E
CC
ω 85.05
-80  0  80
(μm)

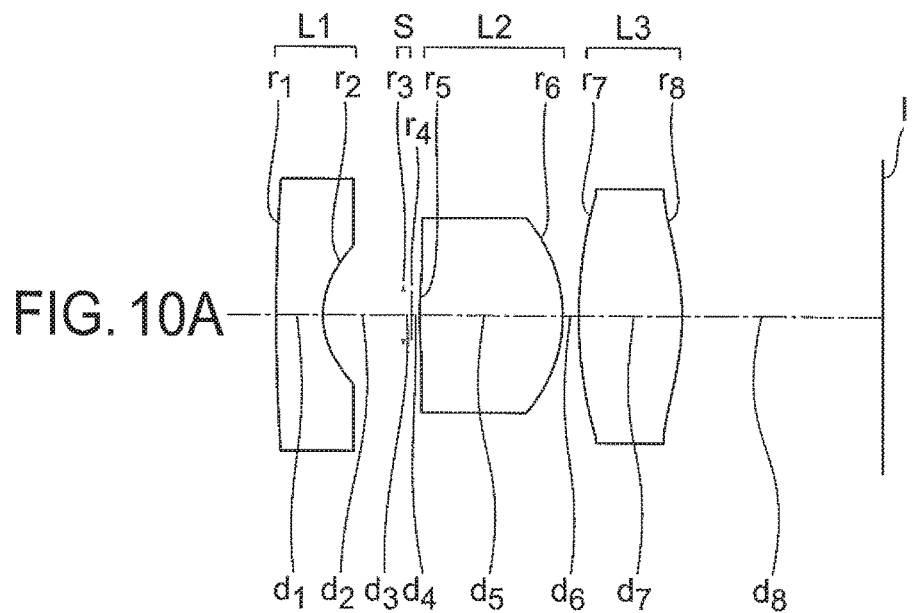
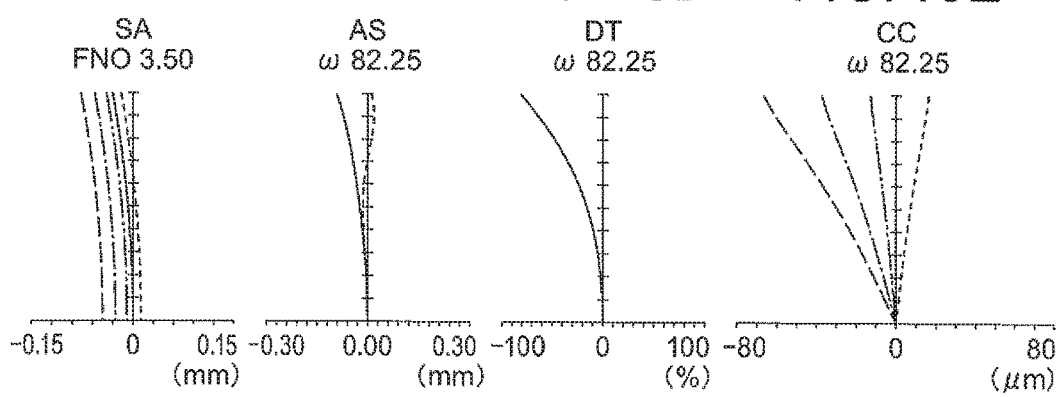

SA
FNO 3.50
-0.15  0  0.15
(mm)

AS
ω 82.25
-0.30  0.00  0.30
(mm)

DT
ω 82.25
-100  0  100
(%)

CC
ω 82.25
-80  0  80
(μm)

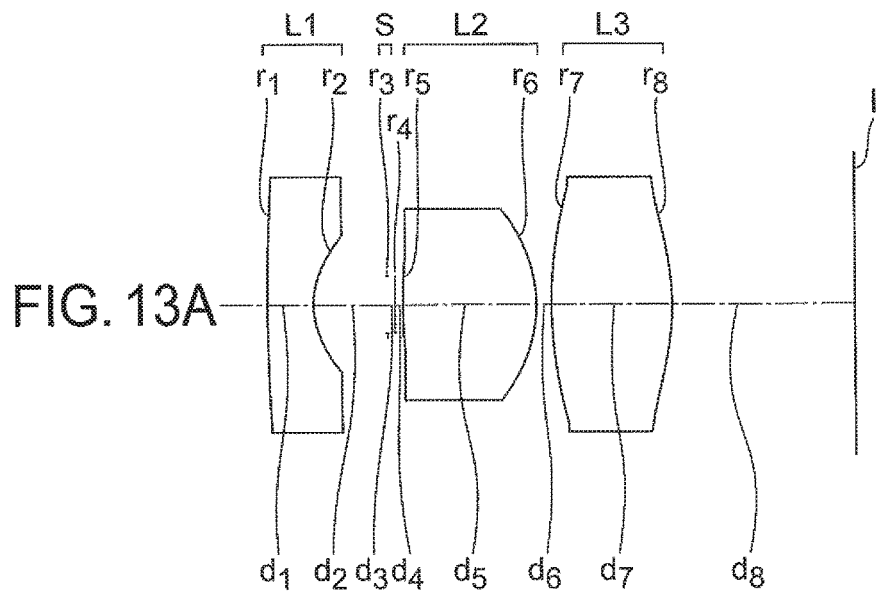
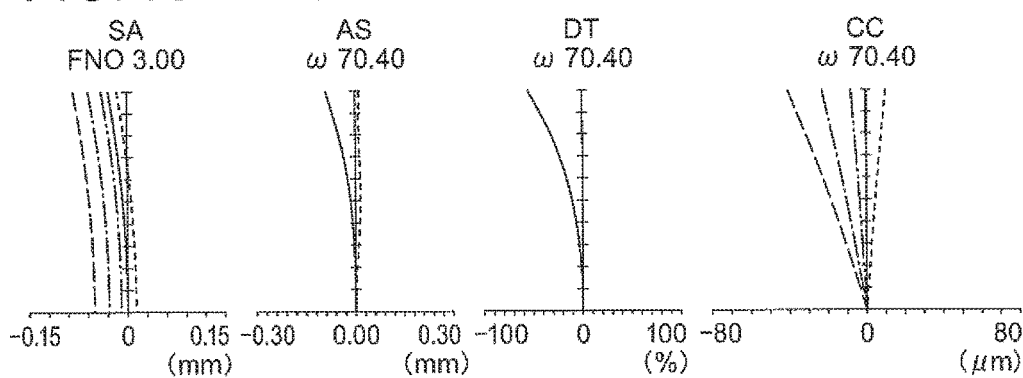

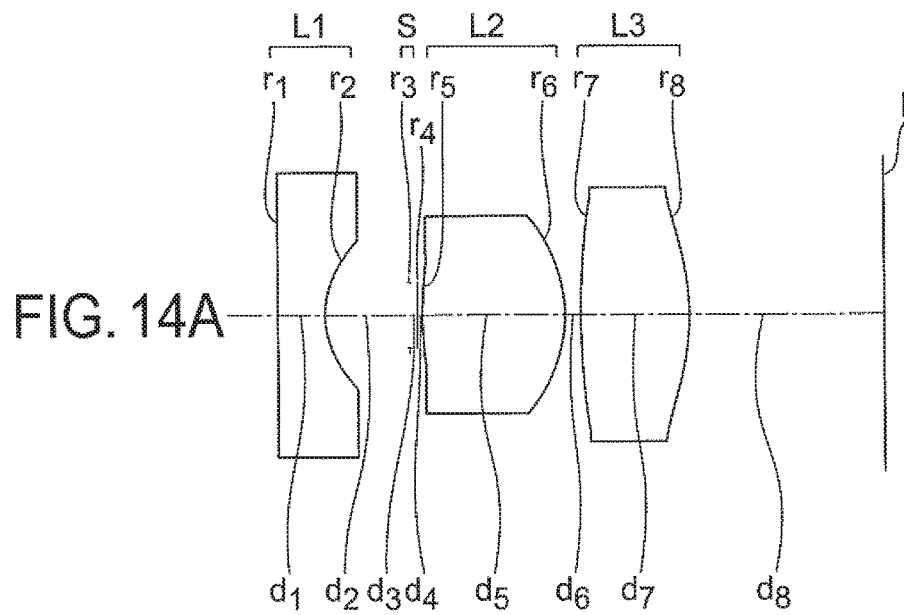
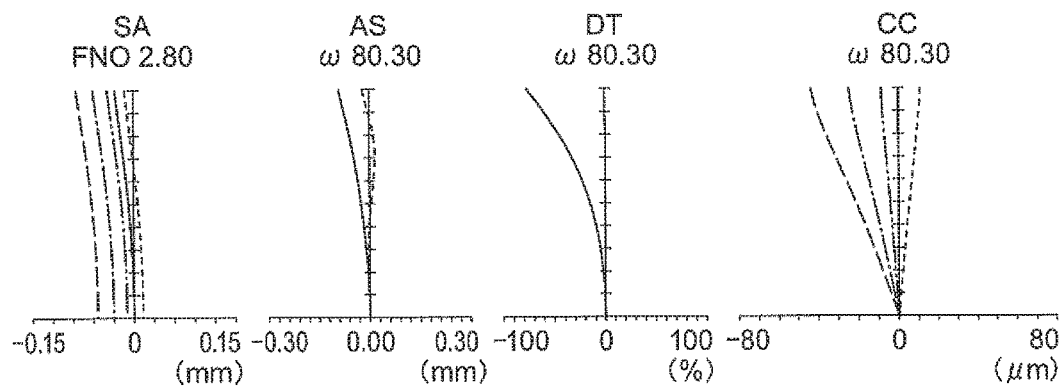

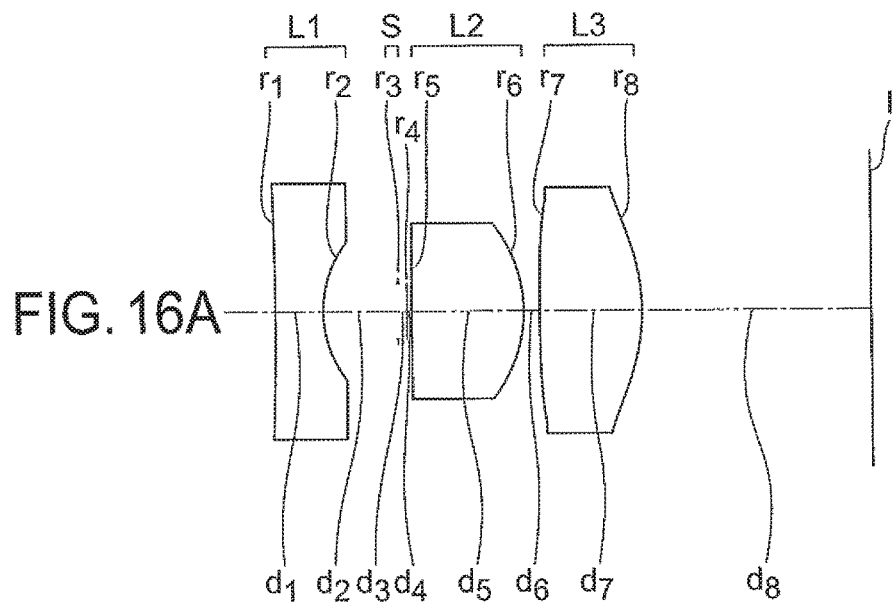
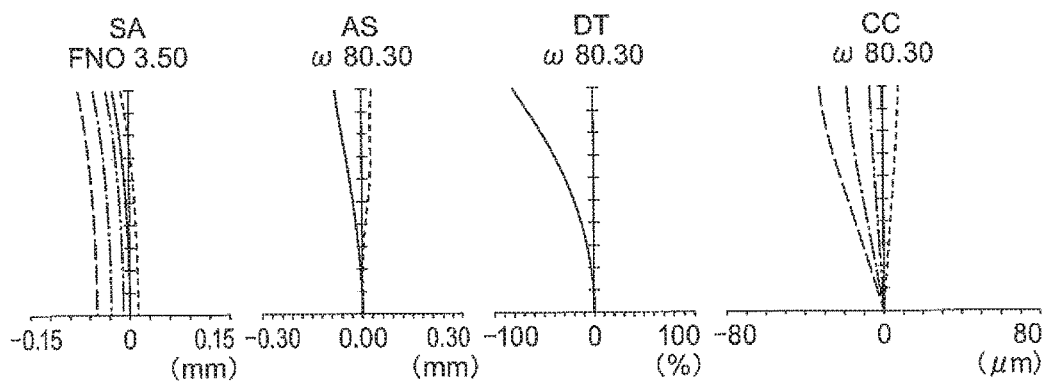

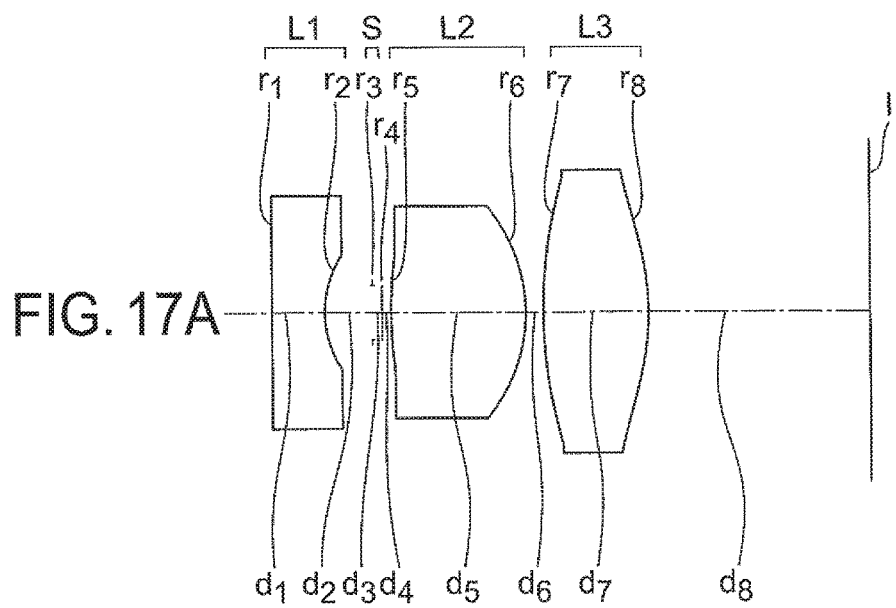
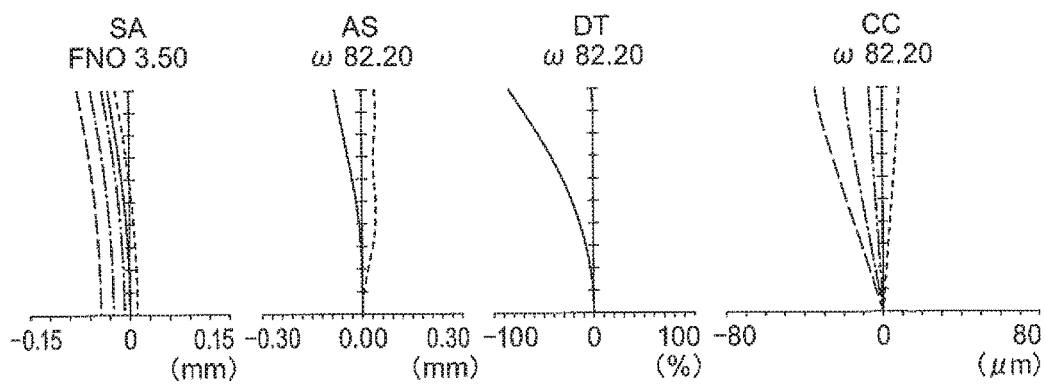

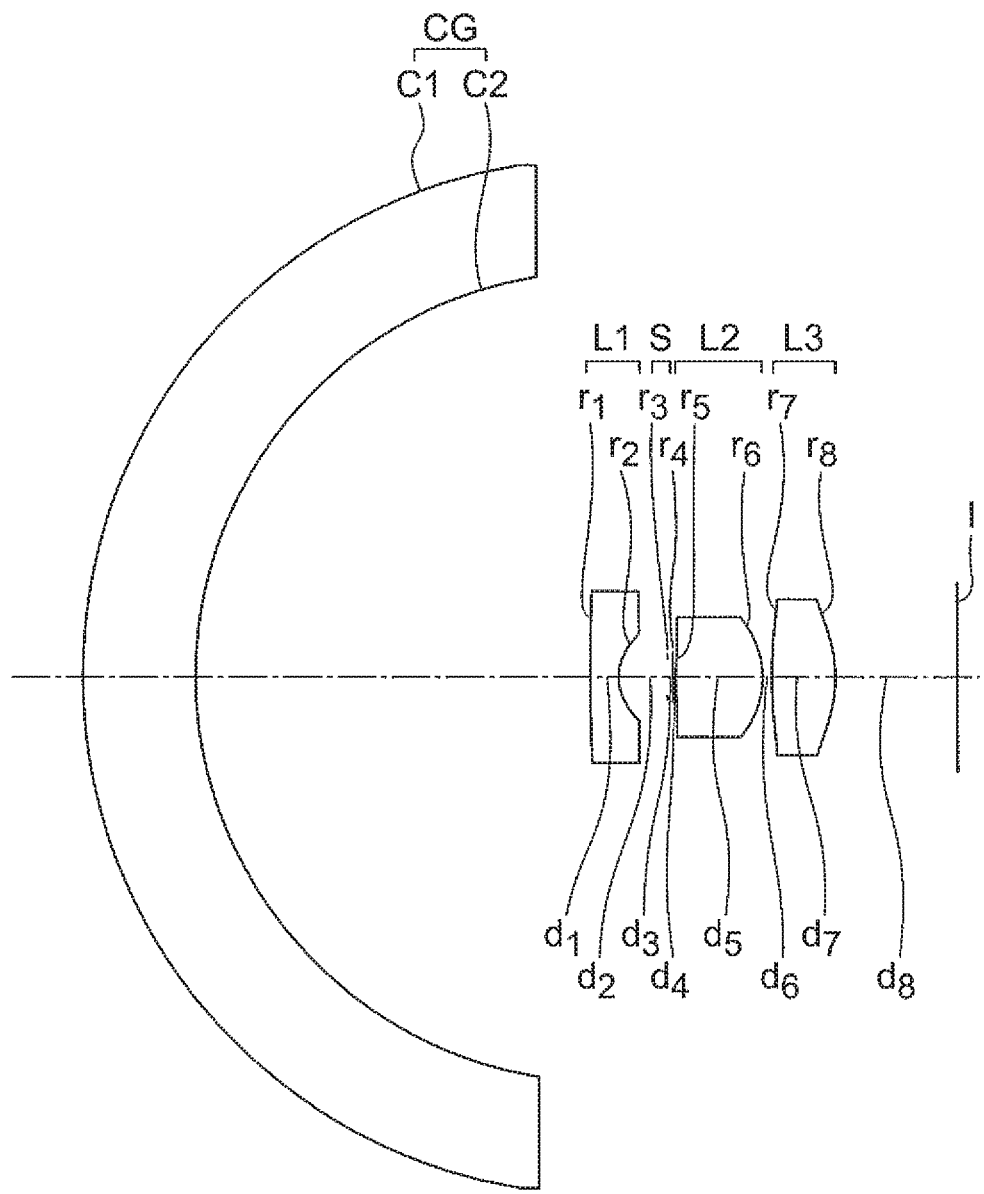

IMAGE PICKUP APPARATUS AND OPTICAL APPARATUS USING THE SAME

CROSS-REFERENCE TO RELATED APPLICATION

The present application is a continuation application of International Application No. PCT/JP2015/078897 filed on Oct. 13, 2015, the entire contents of which are incorporated herein by reference.

BACKGROUND OF THE INVENTION

Field of the Invention

The present invention relates to an image pickup apparatus and an optical apparatus using the same.

Description of the Related Art

For capturing a wide range, an image pickup apparatus which includes an objective optical system having a wide angle of view, and an image sensor has been proposed. A CCD (charge coupled device) or CMOS (complementary metal-oxide semiconductor) etc. are used in the image sensor. In recent years, small-sizing and making the number of pixels large, have been progressing in image sensors. With this, a small-sizing of an objective optical system to be used in an image pickup apparatus has been sought.

Especially, small-sizing has been sought in an image pickup apparatus that is to be mounted in optical apparatuses such as an endoscope having a scope unit (hereinafter, referred to as 'scope type endoscope'), a capsule endoscope, and a digital camera. For this, in these optical apparatuses, small-sizing of an objective optical system has been desired. Furthermore, in a scope type endoscope and a capsule endoscope, cost reduction of the objective optical system has been desired.

For reducing the cost, it is preferable not only to reduce the number of lenses but also to use an inexpensive material for lenses. Glass and resins have been known as a material of lenses. Out of these materials, resins are comparatively inexpensive. For such reason, it is preferable to use a resin as a material of lens.

However, for resins, the lower the price, smaller is a refractive index in many cases. The smaller the refractive index of a lens, more difficult it is to widen the angle of view and to make the size small. For such reasons, even when a resin having a comparatively small refractive index is used, it is necessary to devise an idea to enable widening of the angle of view and small-sizing.

As an objective optical system that is to be mounted in a scope type endoscope, a capsule endoscope, and a digital camera etc., an optical system which includes a small number of lenses has been known.

In Japanese Patent No. 4406299, an objective lens for a small-sized endoscope, which includes three lenses, has been disclosed. The objective lens for endoscope includes in order from an object side, a first lens having a negative refractive power, an optical aperture, a second lens having a positive refractive power, and a third lens having a positive refractive power.

In this objective lens for endoscope, by using a glass having a high refractive index for the first lens, an off-axis aberration such as a curvature of field is corrected favorably while making a lens diameter small. Accordingly, in this objective lens for endoscope, it is possible to achieve a favorable optical performance.

In Japanese Patent No. 4843121, an objective optical system which includes three lenses has been disclosed. The objective optical system includes in order from an object side, a first lens having a negative refractive power, an optical aperture, a second lens having a positive refractive power, and a third lens. The third lens has either a positive refractive power or a negative refractive power.

In this objective optical system, by using a resin for a material of all lenses, a small-sized and light-weight optical system is realized at a low cost.

SUMMARY OF THE INVENTION

An image pickup apparatus of the present invention comprises:
an optical system which includes a plurality of lenses, and
an image sensor which is disposed at an image position of the optical system, wherein
the optical system includes in order from an object side,
a first lens having a negative refractive power,
an aperture stop,
a second lens having a positive refractive power, and
a third lens having a positive refractive power, and
each of the first lens, the second lens, and the third lens is formed of a material having a refractive index not higher than 1.70, and
the following conditional expressions (1), (2), (3), and (4) are satisfied:

$$0 < f3/f2 \leq 1.7 \quad (1),$$

$$0.5 < \Phi 1L/IH < 3.0 \quad (2),$$

$$0.05 < D1R2L/\Sigma d < 0.5 \quad (3), \text{ and}$$

$$-0.4 < f1/R1L < 0.2 \quad (4),$$

where,
f2 denotes a focal length of the second lens,
f3 denotes a focal length of the third lens,
IH denotes a maximum image height,
$\Phi 1L$ denotes an effective aperture at an object-side surface of the first lens,
D1R2L denotes an air space from an image-side surface of the first lens up to an object-side surface of the second lens,
$\Sigma d$ denotes a distance from the object-side surface of the first lens up to a lens surface positioned nearest to image,
f1 denotes a focal length of the first lens, and
R1L denotes a paraxial radius of curvature of the object-side surface of the first lens.

Moreover, an optical apparatus of the present invention comprises
an image pickup apparatus, and
a signal processing circuit.

BRIEF DESCRIPTION OF THE DRAWINGS

FIG. 1A, and FIG. 1B, FIG. 1C, FIG. 1D, and FIG. 1E are a cross-sectional view and aberration diagrams of an optical system of an example 1;

FIG. 2A, and FIG. 2B, FIG. 2C, FIG. 2D, and FIG. 2E are a cross-sectional view and aberration diagrams of an optical system of an example 2;

FIG. 3A, and FIG. 3B, FIG. 3C, FIG. 3D, and FIG. 3E are a cross-sectional view and aberration diagrams of an optical system of an example 3;

FIG. 4A, and FIG. 4B, FIG. 4C, FIG. 4D, and FIG. 4E are a cross-sectional view and aberration diagrams of an optical system of an example 4;

FIG. 6A, and FIG. 6B, FIG. 6C, FIG. 6D, and FIG. 6E are a cross-sectional view and aberration diagrams of an optical system of an example 6;

FIG. 7A, and FIG. 7B, FIG. 7C, FIG. 7D, and FIG. 7E are a cross-sectional view and aberration diagrams of an optical system of an example 7;

FIG. 9A, and FIG. 9B, FIG. 9C, FIG. 9D, and FIG. 9E are a cross-sectional view and aberration diagrams of an optical system of an example 9;

FIG. 10A, and FIG. 10B, FIG. 10C, FIG. 10D, and FIG. 10E are a cross-sectional view an aberration diagrams of an optical system of an example 10;

FIG. 13A, and FIG. 13B, FIG. 13C, FIG. 13D, and FIG. 13E are a cross-sectional view and aberration diagrams of an optical system of an example 13;

FIG. 14A, and FIG. 14B, FIG. 14C, FIG. 14D, and FIG. 14E are a cross-sectional view and aberration diagrams of an optical system of an example 14;

FIG. 16A, and FIG. 16B, FIG. 16C, FIG. 16D, and FIG. 16E are a cross-sectional view and aberration diagrams of an optical system of an example 16;

FIG. 17A, and FIG. 17B, FIG. 17C, FIG. 17D, and FIG. 17E are a cross-sectional view and aberration diagrams of an optical system of an example 17;

FIG. 21 is a cross-sectional view of an optical system of an example 21;

DETAILED DESCRIPTION OF THE INVENTION

Figure 5A:
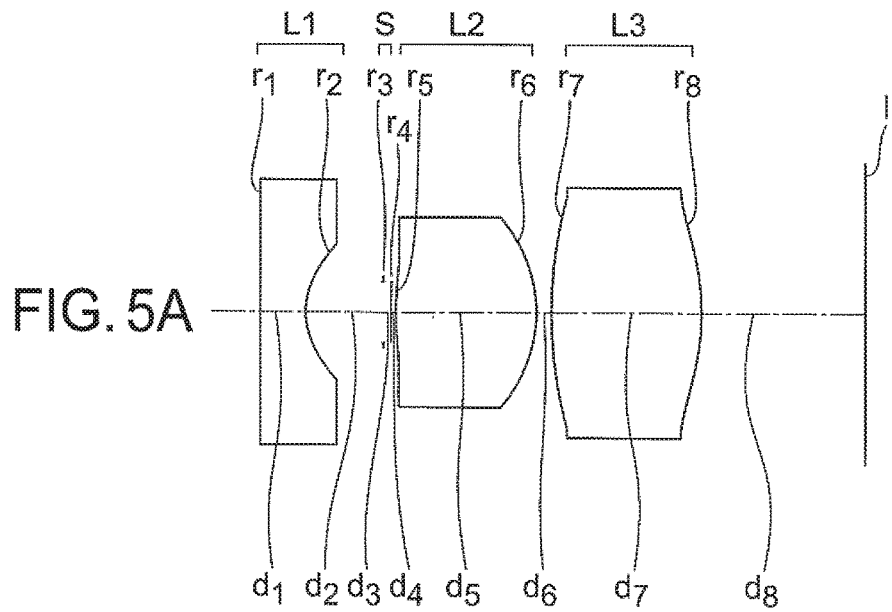
FIG. 5A, and FIG. 5B, FIG. 5C, FIG. 5D, and FIG. 5E are a cross-sectional view and aberration diagrams of an optical system of an example 5.
Figure 5B:
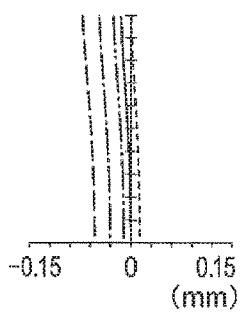
Figure 5C:
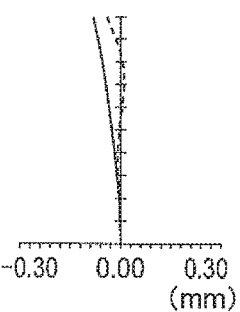
Figure 5D:
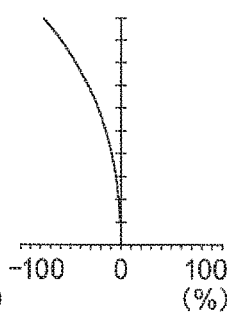
Figure 5E:
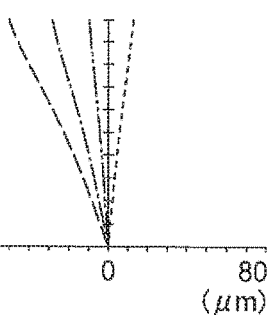
Figure 8A:
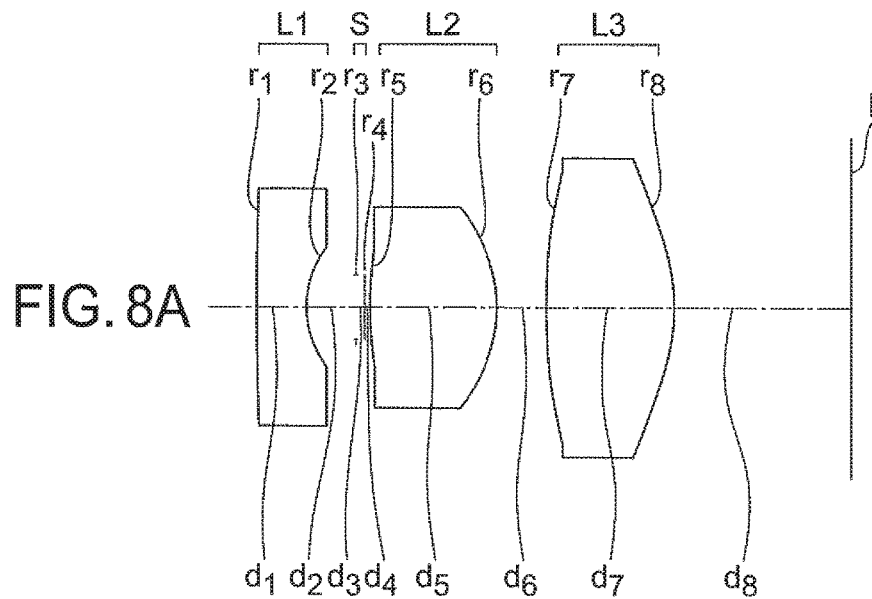
FIG. 8A, and FIG. 8B, FIG. 8C, FIG. 8D, and FIG. 8E are a cross-sectional view and aberration diagrams of an optical system of an example 8.
Figures 8B, 8C, 8D, 8E:
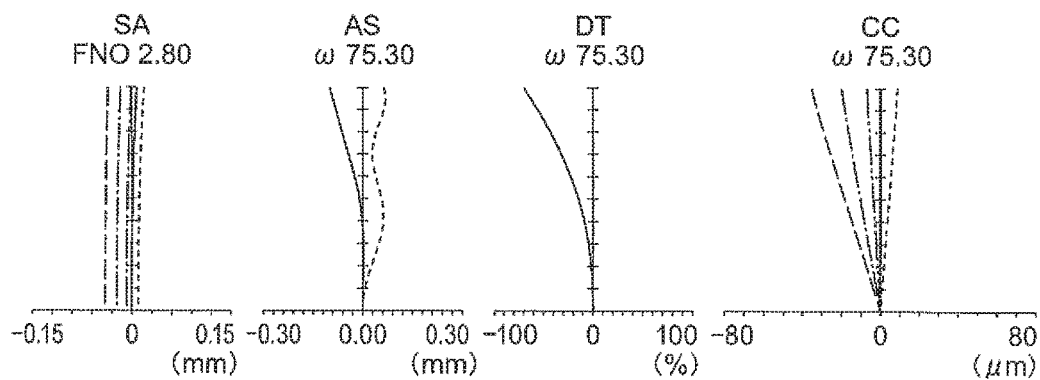
Figure 11A:
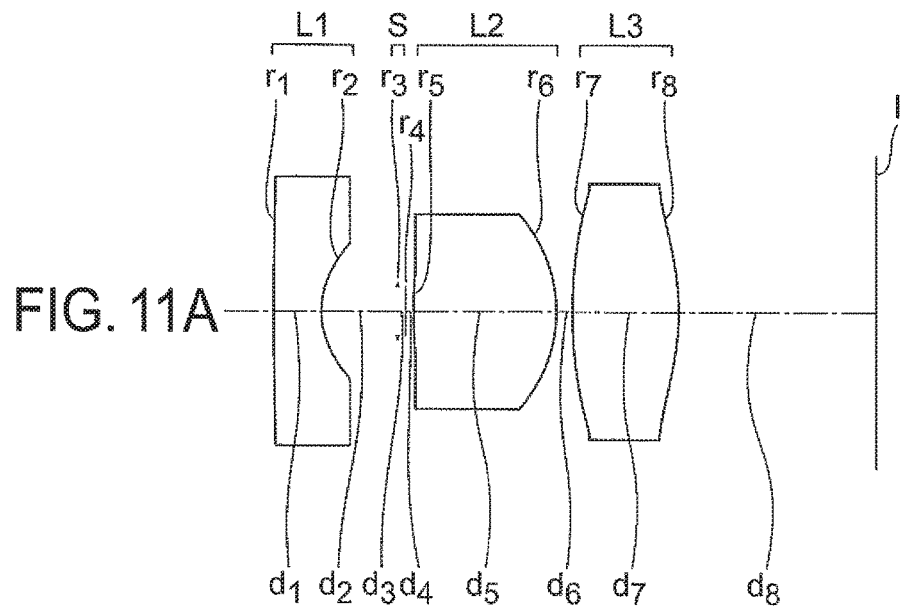
FIG. 11A, and FIG. 11B, FIG. 11C, FIG. 11D, and FIG. 11E are a cross-sectional view and aberration diagrams of an optical system of an example 11.
Figure 11B:
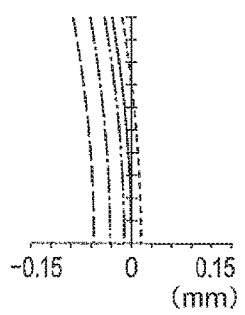
Figure 11C:
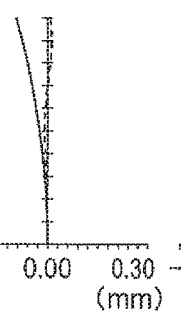
Figure 11D:
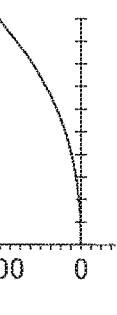
Figure 11E:
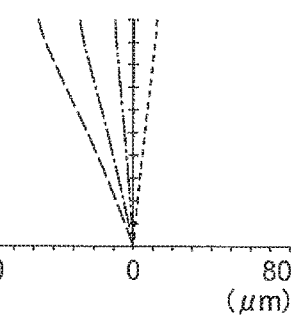
Figure 12A:
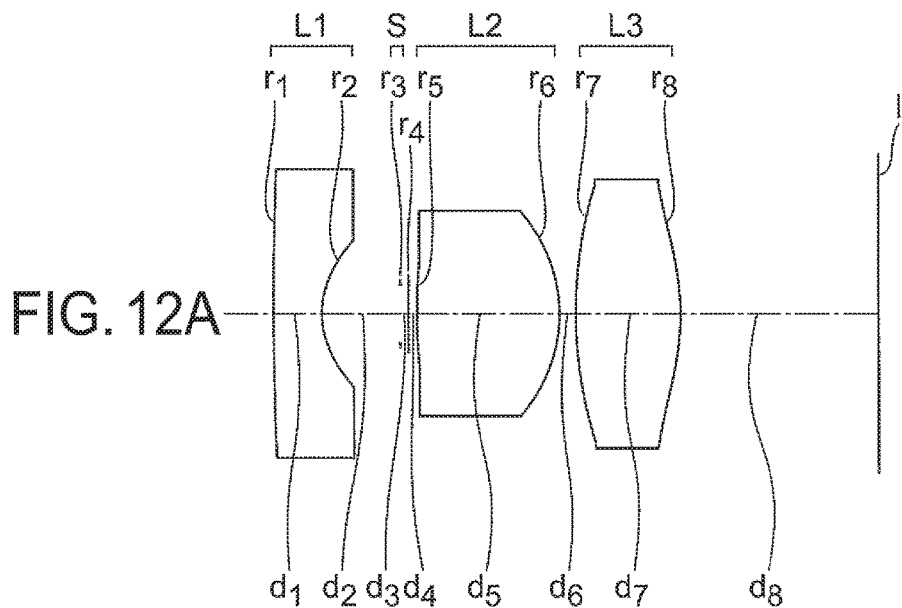
FIG. 12A, and FIG. 12B, FIG. 12C, FIG. 12D, and FIG. 12E are a cross-sectional view and aberration diagrams of an optical system of an example 12.
Figures 12B, 12C, 12D, 12E:
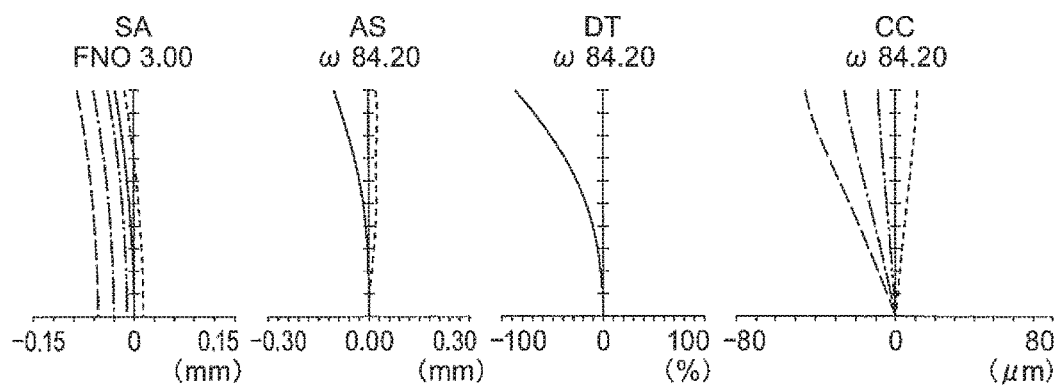
Figure 15A:
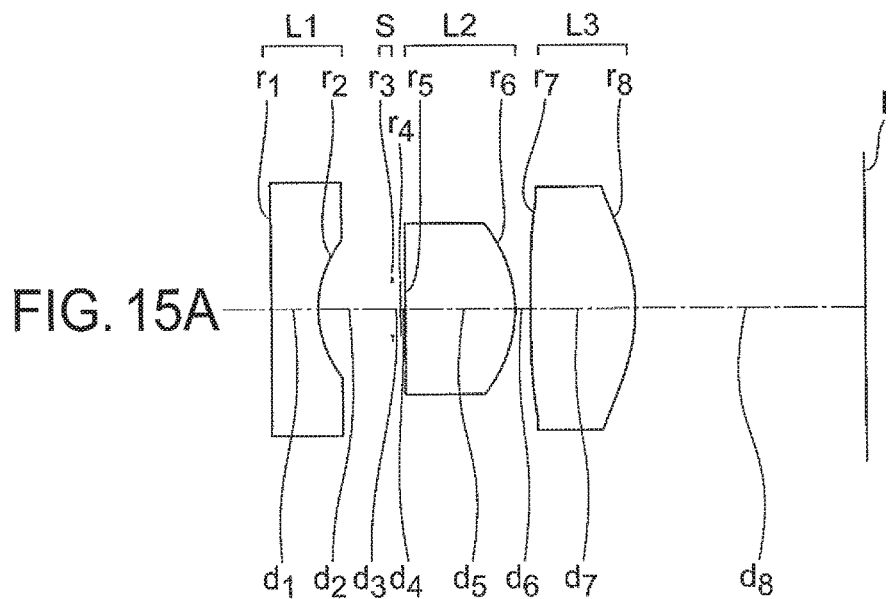
FIG. 15A, and FIG. 15B, FIG. 15C, FIG. 15D, and FIG. 15E are a cross-sectional view and aberration diagrams of an optical system of an example 15.
Figures 15B, 15C, 15D, 15E:
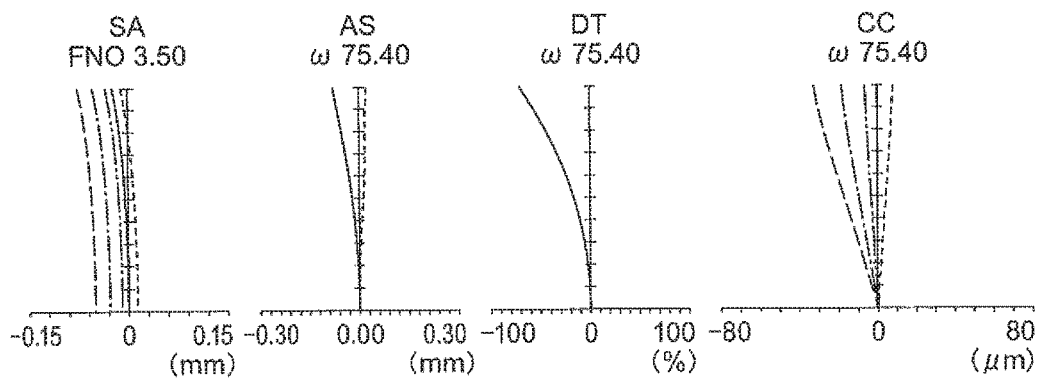
Figure 18A:
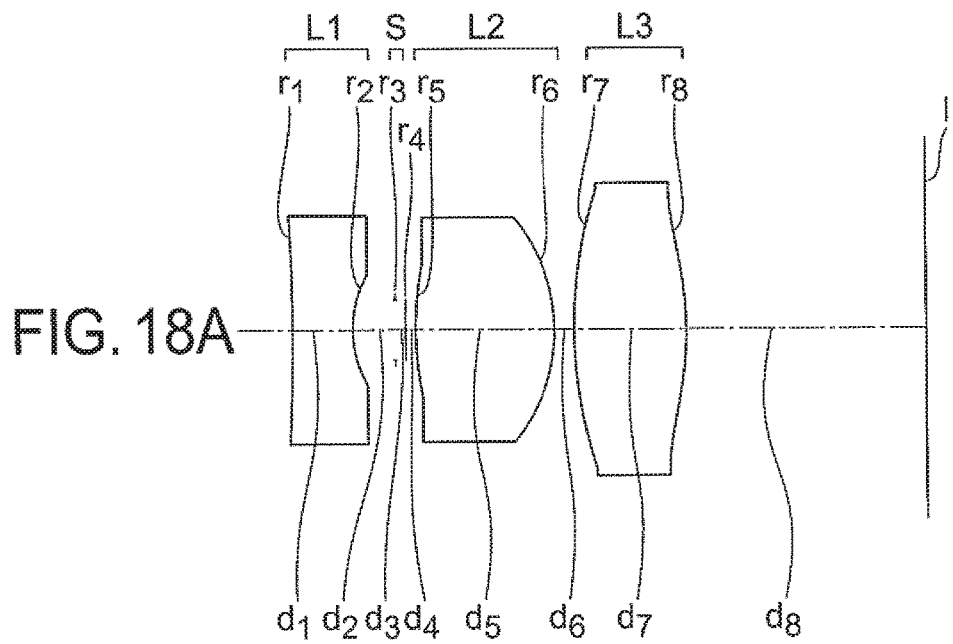
FIG. 18A, and FIG. 18B, FIG. 18C, FIG. 18D, and FIG. 18E are a cross-sectional view and aberration diagrams of an optical system of an example 18.
Figures 18B, 18C, 18D, 18E:
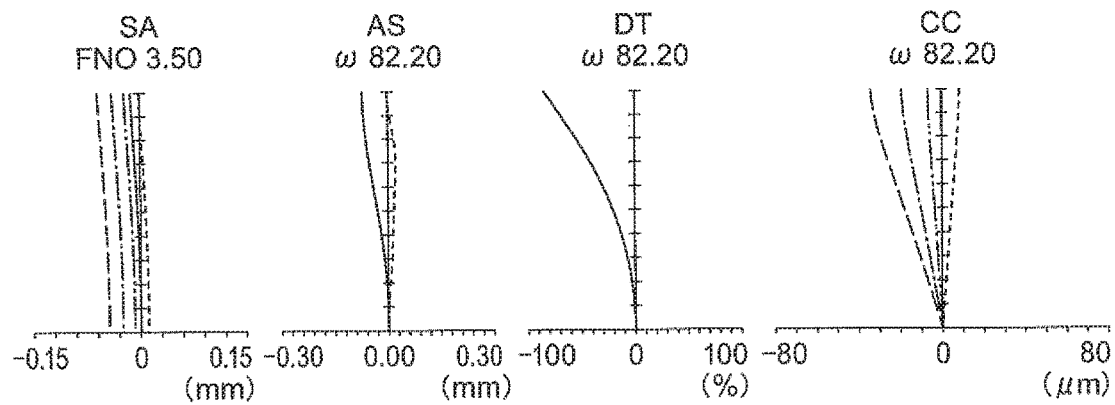
Figure 19A:
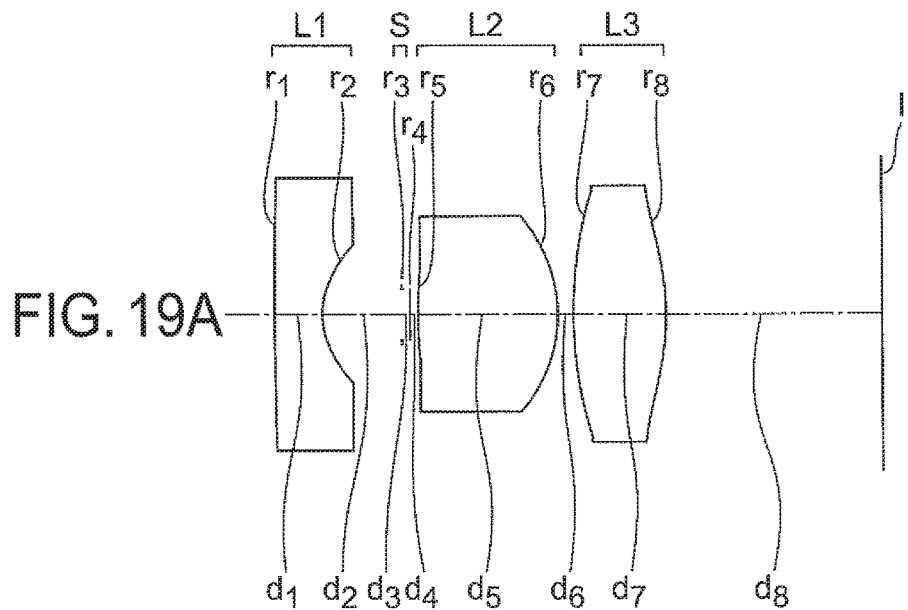
FIG. 19A, and FIG. 19B, FIG. 19C, FIG. 19D, and FIG. 19E are a cross-sectional view and aberration diagrams of an optical system of an example 19.
Figures 19B, 19C, 19D, 19E:
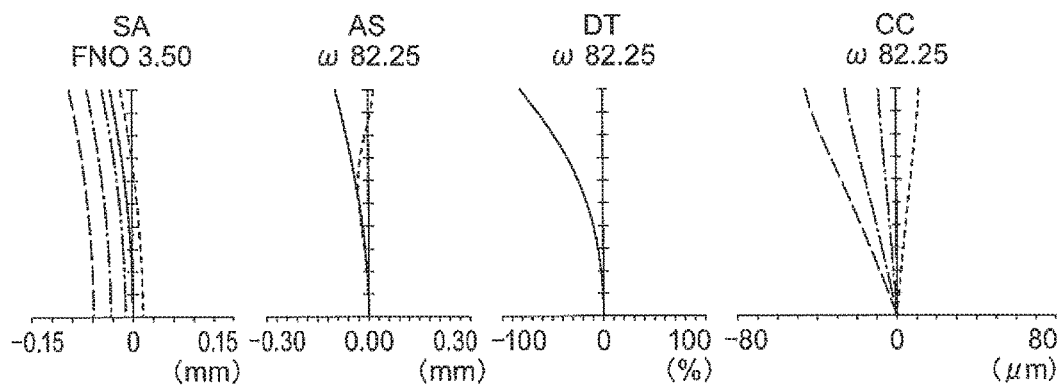
Figure 20A:
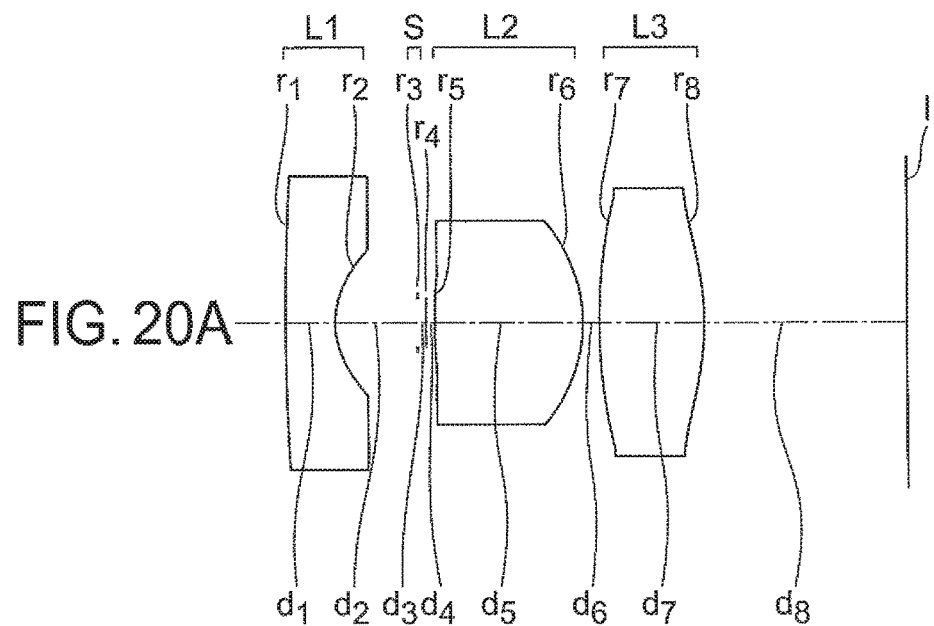
FIG. 20A, and FIG. 20B, FIG. 20C, FIG. 20D, and FIG. 20E are a cross-sectional view and aberration diagrams of an optical system of an example 20.
Figures 20B, 20C, 20D, 20E:
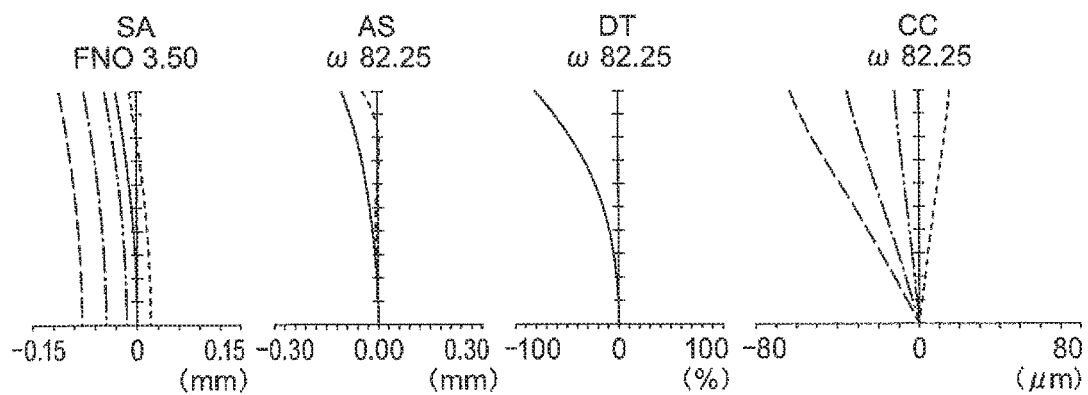

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

An image pickup apparatus of the present embodiment includes an optical system which includes a plurality of lenses, and an image sensor which is disposed at an image position of the optical system, wherein the optical system includes in order from an object side, a first lens having a negative refractive power, an aperture stop, a second lens having a positive refractive power, and a third lens having a positive refractive power, and each of the first lens, the second lens, and the third lens is formed of a material having a refractive index not higher than 1.70, and the following conditional expressions (1), (2), (3), and (4) are satisfied:

$$0 < f3/f2 \leq 1.7 \tag{1},$$

$$0.5 < \Phi 1L/IH < 3.0 \tag{2},$$

$$0.05 < D1R2L/\Sigma d < 0.5 \tag{3, and}$$

$$-0.4 \leq f1/R1L < 0.2 \tag{4},$$

where, f2 denotes a focal length of the second lens, f3 denotes a focal length of the third lens, IH denotes a maximum image height, Φ1L denotes an effective aperture at an object-side surface of the first lens, D1R2L denotes an air space from an image-side surface of the first lens up to an object-side surface of the second lens, Σd denotes a distance from the object-side surface of the first lens up to a lens surface positioned nearest to image, f1 denotes a focal length of the first lens, and R1L denotes a paraxial radius of curvature of the object-side surface of the first lens.

In the optical system of the image pickup apparatus according to the present embodiment, a lens having a negative refractive power is used for the first lens. Accordingly, it is possible to secure a wide angle of view.

In a case in which the first lens is configured by a lens having a negative refractive power, a curvature of field and a chromatic aberration occur in the first lens. Therefore, by disposing a lens having a positive refractive power on the image side of the first lens, the curvature of field and the chromatic aberration are corrected favorably.

Specifically, the second lens having a positive refractive power and the third lens having a positive refractive power are disposed on the image side of the first lens. Accordingly, it is possible to correct the curvature of field and the chromatic aberration favorably.

Moreover, each of the first lens, the second lens, and the third lens is made of a material having the refractive index not higher than 1.70. By making an arrangement such that the refractive index of the material of each lens does not exceed 1.70, it is possible to suppress a fluctuation in a focal position due to a temperature change and a manufacturing error of the refractive index.

Moreover, in the image pickup apparatus of the present embodiment, the abovementioned conditional expressions (1), (2), (3), and (4) are satisfied.

By making an arrangement such that a value does not fall below a lower limit value of conditional expression (1), it is possible to maintain the refractive power of the third lens to be appropriate even when the angle of view is widened.

Consequently, it is possible to correct both the curvature of field and an astigmatism favorably.

By making an arrangement such that the value does not exceed an upper limit value of conditional expression (1), it is possible to maintain the refractive power of the second lens to be appropriate. Consequently, it is possible to suppress an occurrence of a spherical aberration and a coma. Moreover, for suppressing the occurrence of the coma in particular, it is preferable to make a radius of curvature of an image-side surface small with respect to a radius of curvature of an object-side surface. Even in a case when such an arrangement is made, since the radius of curvature of the image-side surface does not becomes excessively small, it is possible to maintain a workability of the second lens to be favorable.

By making an arrangement such that a value does not fall below a lower limit value of conditional expression (2), in the first lens, it is possible to separate a position through which an axial light beam passes and a position through which an off-axis light beam passes. As a result, it is possible to correct the curvature of field favorably.

By making an arrangement such that the value does not exceed an upper limit value of conditional expression (2), it is possible to suppress a diameter of the first lens to be small. As a result, it is possible to make the optical system small-sized.

By making an arrangement such that a value does not fall below a lower limit value of conditional expression (3), it is possible to shorten the total length of the optical system, as well as to realize widening of the angle of view. Moreover, in the first lens, it is possible to separate the position through which the axial light ray passes and the position through which the off-axis light ray passes. As a result, it is possible to correct the curvature of field favorably.

By making an arrangement such that the value does not exceed an upper limit value of conditional expression (3), it is possible to secure a thickness of each lens appropriately, as well as to shorten the total length of the optical system. Furthermore, it is possible to make the diameter of the first lens small.

The refractive power at the object-side surface of the first lens can be let to be any of the negative refractive power and the positive refractive power.

In a case of letting the refractive power at the object-side surface of the first lens to be the positive refractive power, an arrangement is to be made such that a value does not fall below a lower limit value of conditional expression (4). By making such arrangement, since the positive refractive power at the object-side surface of the first lens does not become excessively large, it is possible to suppress an increase in the negative refractive power at the image-side surface of the first lens. Therefore, it is possible to suppress an occurrence of an astigmatism.

Moreover, when the value falls below the lower limit value of conditional expression (4), since the negative refractive power at the image-side surface of the first lens increases, the radius of curvature of the image-side surface of the first lens becomes small. In this case, a thickness of a lens periphery (hereinafter, referred to as 'peripheral thickness') becomes thick. By making the arrangement such that the value does not fall below the lower limit value of conditional expression (4), it is possible to suppress an increase in the peripheral thickness. As a result, it is possible to maintain the workability of the first lens to be appropriate.

In a case of letting the refractive power at the object-side surface of the first lens to be the negative refractive power, an arrangement is to be made such that the value does not exceed an upper limit value of conditional expression (4). By making such arrangement, a large refraction of an off-axis principal light ray incident on the object-side surface of the first lens is suppressed. Consequently, it is possible to suppress a negative distortion in particular from increasing further.

It is preferable that the following conditional expression (1') be satisfied instead of conditional expression (1).

$$0.40 < f3/f2 \leq 1.70 \tag{1'}$$

It is more preferable that the following conditional expression (1") be satisfied instead of conditional expression (1).

$$0.80 < f3/f \leq 1.70 \tag{1"}$$

It is preferable that the following conditional expression (2') be satisfied instead of conditional expression (2).

$$0.54 < \Phi 1L/IH < 2.20 \tag{2'}$$

It is more preferable that the following conditional expression (2") be satisfied instead of conditional expression (2).

$$0.58 < \Phi 1L/IH < 1.40 \tag{2"}$$

It is preferable that the following conditional expression (3') be satisfied instead of conditional expression (3).

$$0.08 < D1R2L/\Sigma d < 0.40 \tag{3'}$$

It is more preferable that the following conditional expression (3") be satisfied instead of conditional expression (3).

$$0.11 < D1R2L/\Sigma d < 0.30 \tag{3"}$$

It is preferable that the following conditional expression (4') be satisfied instead of conditional expression (4)

$$-0.310 < f1/R1L < 0.170 \tag{4'}$$

It is more preferable that the following conditional expression (4") be satisfied instead of conditional expression (4).

$$-0.220 < f1/R1L < 0.140 \tag{4"}$$

In such manner, the optical system of the image pickup apparatus of the present embodiment, while being small-sized and light-weight, has a wide angle of view and an appropriate back focus, and in which an off-axis aberration is corrected favorably. Therefore, according to the optical system of the image pickup apparatus of the present embodiment, an optical image with a high resolution and wide angle of view is achieved, while being small-sized and light-weight. Moreover, according to the image pickup apparatus of the present embodiment, it is possible to realize an image pickup apparatus equipped with an optical system which has a wide angle of view and an appropriate back focus, and in which an off-axis aberration is corrected favorably, while being small-sized and light-weight.

In the image pickup apparatus of the present embodiment, it is preferable that the following conditional expression (5) be satisfied:

$$\alpha max - \alpha min < 4.0 \times 10^{-5}/°C. \tag{5}$$

where, $\alpha$ max denotes a largest coefficient of linear expansion among coefficients of linear expansion at 20 degrees of the plurality of lenses, and $\alpha$ min denotes a smallest coefficient of linear expansion among the coefficients of linear expansion at 20 degrees of the plurality of lenses.

Conditional expression (5) is an expression in which a difference in the coefficient of linear expansion of the two lenses is taken. The coefficient of linear expansion is a coefficient of linear expansion at 20 degrees. The optical system of the present embodiment includes the plurality of lenses. In each of the plurality of lenses, a shape and a refractive index of lens varies with a change in temperature. Therefore, a focal length changes in each lens with the change in temperature.

Therefore, by satisfying conditional expression (5), it is possible to keep the focal length substantially constant as the overall optical system even when the focal length changes in each lens with the change in temperature. As a result, it is possible to suppress a fluctuation in aberration, and particularly a fluctuation in a spherical aberration and a fluctuation in a curvature of field. Moreover, it is possible to make a fluctuation in a focal position small.

It is preferable that the following conditional expression (5') be satisfied instead of conditional expression (5).

$$0.00/° C.<\alpha max-\alpha min<2.00\times 10^{-5}/° C. \quad (5')$$

It is more preferable that the following conditional expression (5") be satisfied instead of conditional expression (5).

$$1.00\times 10^{-6}/° C.<\alpha max-\alpha min<1.00\times 10^{-5}/° C. \quad (5")$$

In the image pickup apparatus of the present embodiment, it is preferable that the following conditional expression (6) be satisfied:

$$-3.0<f1/FL<-0.05 \quad (6),$$

where, f1 denotes the focal length of the first lens, and

FL denotes a focal length of the overall optical system.

By making an arrangement such that a value does not fall below a lower limit value of conditional expression (6), it is possible to prevent an increase in the diameter of the first lens.

When an attempt is made to secure the appropriate back focus at the time of widening the angle of view, a distance between the aperture stop and the first lens becomes long. As a result, the diameter of the first lens increases. By making the arrangement such that the value does not fall below the lower limit value of conditional expression (6), it is possible to prevent the increase in the diameter of the first lens.

By making an arrangement such that the value does not exceed an upper limit value of conditional expression (6), the negative refractive power of the first lens does not become excessively large. As a result, it is possible to suppress the curvature of field from occurring unduly substantially.

It is more preferable that the following conditional expression (6') be satisfied instead of conditional expression (6).

$$-2.50<f1/FL<-0.07 \quad (6')$$

It is even more preferable that the following conditional expression (6") be satisfied instead of conditional expression (6).

$$-2.00<f1/FL<-0.09 \quad (6")$$

In the image pickup apparatus of the present embodiment, it is preferable that the following conditional expression (7) be satisfied:

$$1.0<f2/FL<3.0 \quad (7),$$

where, f2 denotes the focal length of the second lens, and

FL denotes the focal length of the overall optical system.

By making an arrangement such that a value does not fall below a lower limit value of conditional expression (7), it is possible to suppress an occurrence of the spherical aberration and an occurrence of the coma. By making an arrangement such that the value does not exceed an upper limit value of conditional expression (7), it is possible to correct the astigmatism and the curvature of field favorably.

When the value exceeds the upper limit value of conditional expression (7), the positive refractive power of the second lens becomes excessively small. In this case, for securing a wide angle of view and an appropriate back focus, the positive refractive power of the third lens is to be made large.

However, when the positive refractive power of the third lens is made large, the astigmatism and the curvature of field occur substantially. By making an arrangement such that the value does not exceed the upper limit value of conditional expression (7), it is possible to suppress the positive refractive power of the third lens from becoming excessively large. Consequently, it is possible to correct the astigmatism and the curvature of field favorably.

It is more preferable that the following conditional expression (7') be satisfied instead of conditional expression (7).

$$1.10<f2/FL<2.70 \quad (7')$$

It is even more preferable that the following conditional expression (7") be satisfied instead of conditional expression (7).

$$1.20<f2/FL<2.40 \quad (7")$$

In the image pickup apparatus of the present embodiment, it is preferable that the following conditional expression (8) be satisfied:

$$1.0<\Sigma d/FL<6.0 \quad (8),$$

where, $\Sigma d$ denotes the distance from the object-side surface of the first lens up to the lens surface positioned nearest to image, and FL denotes the focal length of the overall optical system.

Conditional expression (8) is a conditional expression related to a ratio of the total length of the optical system and the focal length of the overall optical system. By satisfying conditional expression (8), it is possible to achieve small-sizing and widening of the angle of view of the optical system.

By making an arrangement such that a value does not fall below a lower limit value of conditional expression (8), it is possible to prevent a distance between the lenses from becoming narrow. Accordingly, since it is possible to maintain a distance between the lenses to be appropriate, it is possible to separate a position through which the axial light beam passes and a position through which the off-axis light beam passes in the first lens and the third lens in particular. As a result, it is possible to correct the curvature of field favorably, and moreover, it is possible to prevent further increase in the distortion.

By making an arrangement such that the value does not exceed an upper limit value of conditional expression (8), it is possible to maintain the distance between the lenses to be appropriate, as well as to make a diameter of each lens small, even when the angle of view is widened.

It is more preferable that the following conditional expression (8') be satisfied instead of conditional expression (8).

$$1.50<\Sigma d/FL<5.20 \quad (8')$$

It is even more preferable that the following conditional expression (8") be satisfied instead of conditional expression (8).

$$2.00<\Sigma d/FL<4.40 \quad (8'')$$

In the image pickup apparatus of the present embodiment, it is preferable that the following conditional expression (9) be satisfied:

$$0.3<vd1/vd2<1.2 \quad (9),$$

where,
vd1 denotes Abbe number for the first lens, and
vd2 denotes Abbe number for the second lens.

By making an arrangement such that a value does not fall below a lower limit value of conditional expression (9), it is possible to correct a chromatic aberration of magnification favorably. By making an arrangement such that the value does not exceed an upper limit value of conditional expression (9), it is possible to correct a longitudinal chromatic aberration favorably.

It is more preferable that the following conditional expression (9') be satisfied instead of conditional expression (9).

$$0.35<vd1/vd2<1.15 \quad (9')$$

It is even more preferable that the following conditional expression (9") be satisfied instead of conditional expression (9).

$$0.40<vd1/vd2<1.10 \quad (9'')$$

In the image pickup apparatus of the present embodiment, it is preferable that the following conditional expression (10) be satisfied:

$$0.8<vd2/vd3<3.0 \quad (10),$$

where,
vd2 denotes Abbe number for the second lens, and
vd3 denotes Abbe number for the third lens.

By making an arrangement such that a value does not fall below a lower limit value of conditional expression (10), it is possible to correct the chromatic aberration of magnification favorably. By making an arrangement such that the value does not exceed an upper limit value of conditional expression (10), it is possible to correct the longitudinal chromatic aberration favorably.

It is more preferable that the following conditional expression (10') be satisfied instead of conditional expression (10).

$$0.85<vd2/vd3<2.90 \quad (10')$$

It is even more preferable that the following conditional expression (10") is satisfied instead of conditional expression (10).

$$0.90<vd2/vd3<2.20 \quad (10'')$$

In the image pickup apparatus of the present embodiment, it is preferable that the following conditional expression (11) be satisfied:

$$0.10<(R2L+R2R)/(R2L-R2R)<2.00 \quad (11),$$

where,
R2L denotes a paraxial radius of curvature of the object-side surface of the second lens, and
R2R denotes a paraxial radius of curvature of the image-side surface of the second lens.

By satisfying conditional expression (11), it is possible to correct a spherical aberration and the coma favorably.

It is more preferable that the following conditional expression (11') be satisfied instead of conditional expression (11).

$$0.15<(R2L+R2R)/(R2L-R2R)<1.70 \quad (11')$$

It is even more preferable that the following conditional expression (11") be satisfied instead of conditional expression (11).

$$0.20<(R2L+R2R)/(R2L-R2R)<1.40 \quad (11'')$$

In the image pickup apparatus of the present embodiment, it is preferable that the following conditional expression (12) be satisfied:

$$2.0<\Sigma d/D\text{maxair}<9.0 \quad (12),$$

where,
$\Sigma d$ denotes the distance from the object-side surface of the first lens up to the lens surface positioned nearest to image, and
Dmaxair denotes a largest air space among air spaces between the object-side surface of the first lens and the lens surface positioned nearest to image.

The air space is a space between the two adjacent lenses. Moreover, in a case in which the aperture stop is positioned between the two adjacent lenses, the air space is a space between the lens and the aperture stop.

By making an arrangement such that a value does not fall below a lower limit value of conditional expression (12), it is possible to keep a thickness of a lens appropriately. As a result, it is possible to make a workability of a lens favorable. By making an arrangement such that the value does not exceed an upper limit value of conditional expression (12), it is possible to suppress the increase in the total length of the optical system. As a result, it is possible to make the optical system small-sized.

Moreover, when the distance between the first lens and the second lens corresponds to Dmaxair, the distance between the first lens and the second lens can be secured to be adequately wide. Consequently, in the first lens, it is possible to separate the position through which an axial light beam passes and the position through which an off-axis light beam passes. As a result, it is possible to correct favorably, an off-axis aberration, and particularly the curvature of field, and moreover, it is possible to prevent the distortion from increasing further.

In such manner, it is preferable to make an arrangement such that the distance between the first lens and the second lens corresponds to Dmaxair. However, an arrangement may be made such that the distance between the second lens and the third lens corresponds to Dmaxair. In this case, since it is possible to secure both of the refractive power of the second lens and the refractive power of the third lens appropriately, it is possible to achieve both of small-sizing and widening of the angle of view of the optical system.

It is more preferable that the following conditional expression (12') be satisfied instead of conditional expression (12).

$$2.60<\Sigma d/D\text{maxair}<8.00 \quad (12')$$

It is even more preferable that the following conditional expression (12") be satisfied instead of conditional expression (12).

$$3.20<\Sigma d/D\text{maxair}<7.00 \quad (12'')$$

In the image pickup apparatus of the present embodiment, it is preferable that the optical system include an aperture stop, and the following conditional expression (13) be satisfied:

$$0.4<D1Ls/FL<2.0 \quad (13),$$

where,

D1Ls denotes a distance on an optical axis from the object-side surface of the first lens up to the apertures stop, and FL denotes the focal length of the overall optical system.

More elaborately, D1Ls is a distance from the object-side surface of the first lens up to an object-side surface of the aperture stop.

By exceeding a lower limit value of conditional expression (13), it is possible to move away the aperture stop from the object-side surface of the first lens. Accordingly, at the first lens, it is possible to separate a position through which an axial light beam passes and a position through which an off-axis light beam passes. As a result, it is possible to correct the curvature of field favorably.

By falling below an upper limit value of conditional expression (13), it is possible to suppress a distance from the first lens up to the aperture stop, to be short. As a result, it is possible to shorten the total length of the optical system.

It is more preferable that the following conditional expression (13') be satisfied instead of conditional expression (13).

$$0.45 < D1Ls/FL < 1.70 \quad (13')$$

It is even more preferable that the following conditional expression (13") be satisfied instead of conditional expression (13).

$$0.50 < D1Ls/FL < 1.40 \quad (13'')$$

In the image pickup apparatus of the present embodiment, it is preferable that the half angle of view be not less than 65 degrees.

By making such arrangement, it is possible to capture a wide range.

It is preferable that the image pickup apparatus of the present embodiment include an optical member through which light passes, on the object side of the optical system, and both surfaces of the optical member be curved surfaces.

It is possible to form two spaces by the optical member. For instance, a closed space is formed by the optical member and another member, and the optical system is disposed in the closed space. By making such arrangement, it is possible to carry out imaging of other space stably, independent of an environment of the other space. Imaging by a capsule endoscope is an example of such imaging.

In a capsule endoscope, imaging of various parts in body is carried out. For imaging, a subject has to swallow the capsule endoscope. Therefore, in the capsule endoscope, it is necessary to make the image pickup apparatus water-tight, as well as to minimize a resistance at the time of swallowing and a friction with each organ in the body. For this, it is possible to meet these requirements by making both surfaces of the optical member curved surfaces. In such manner, by making the abovementioned arrangement, it is possible to use the image pickup apparatus of the present embodiment as an image pickup apparatus of a capsule endoscope. Moreover, even for applications other than imaging inside the body, it is possible to protect the optical system by the optical member.

In the image pickup apparatus of the present embodiment, it is preferable that the following conditional expression (14) be satisfied:

$$30 < |Fc/FL| \quad (14),$$

where,

Fc denotes a focal length of the optical member, and
FL denotes the focal length of the overall optical system.

By satisfying conditional expression (14), it is possible to maintain an imaging performance of the optical system to be favorable even when an accuracy of assembling during manufacturing of the optical system is reduced.

It is more preferable that the following conditional expression (14') be satisfied instead of conditional expression (14).

$$50.00 < |Fc/FL| \quad (14'),$$

An optical apparatus of the present embodiment includes the abovementioned image pickup apparatus and a signal processing circuit.

According to the optical apparatus of the present embodiment, it is possible to achieve an image having a high resolution and a wide angle of view, while being small-sized.

The image pickup apparatus and the optical apparatus described above may satisfy a plurality of arrangements simultaneously. Making such arrangement is preferable for achieving a favorable image pickup apparatus and optical apparatus. Moreover, combinations of preferable arrangements are arbitrary. Furthermore, regarding each conditional expression, only an upper limit value or a lower limit value of a further restricted numerical range of the conditional expression may be restricted.

Examples of an image pickup apparatus according to certain aspects of the present invention will be described below in detail by referring to the accompanying diagrams. However, the present invention is not restricted to the examples described below. An optical system of the image pickup apparatus will be described below. It is assumed that the image sensor is disposed at an image position formed by the optical system.

In diagrams of examples, FIG. 1A, FIG. 2A, FIG. 3A, FIG. 4A, FIG. 5A, FIG. 6A, FIG. 7A, FIG. 8A, FIG. 9A, FIG. 10A, FIG. 11A, FIG. 12A, FIG. 13A, FIG. 14A, FIG. 15A, FIG. 16A, FIG. 17A, FIG. 18A, FIG. 19A, and FIG. 20A are lens cross-sectional views.

FIG. 1B, FIG. 2B, FIG. 3B, FIG. 4B, FIG. 5B, FIG. 6B, FIG. 7B, FIG. 8B, FIG. 9B, FIG. 10B, FIG. 11B, FIG. 12B, FIG. 13B, FIG. 14B, FIG. 15B, FIG. 16B, FIG. 17B, FIG. 18B, FIG. 19B, and FIG. 20B show a spherical aberration (SA).

FIG. 1C, FIG. 2C, FIG. 3C, FIG. 4C, FIG. 5C, FIG. 6C, FIG. 7C, FIG. 8C, FIG. 9C, FIG. 10C, FIG. 11C, FIG. 12C, FIG. 13C, FIG. 14C, FIG. 15C, FIG. 16C, FIG. 17C, FIG. 18C, FIG. 19C, and FIG. 20C show an astigmatism (AS).

FIG. 1D, FIG. 2D, FIG. 3D, FIG. 4D, FIG. 5D, FIG. 6D, FIG. 7D, FIG. 8D, FIG. 9D, FIG. 10D, FIG. 11D, FIG. 12D, FIG. 13D, FIG. 14D, FIG. 15D, FIG. 16D, FIG. 17D, FIG. 18D, FIG. 19D, and FIG. 20D show a distortion (DT).

FIG. 1E, FIG. 2E, FIG. 3E, FIG. 4E, FIG. 5E, FIG. 6E, FIG. 7E, FIG. 8E, FIG. 9E, FIG. 10E, FIG. 11E, FIG. 12E, FIG. 13E, FIG. 14E, FIG. 15E, FIG. 16E, FIG. 17E, FIG. 18E, FIG. 19E, and FIG. 20E show a chromatic aberration of magnification (CC).

An optical system of an example 1 includes in order from an object side, a planoconcave negative lens L1, a positive meniscus lens L2 having a convex surface directed toward an image side, and a biconvex positive lens L3.

An aperture stop S is disposed between the planoconcave negative lens L1 and the positive meniscus lens L2.

An aspheric surface is provided to a total of five surfaces which are, an image-side surface of the planoconcave negative lens L1, both surfaces of the positive meniscus lens L2, and both surfaces of the biconvex positive lens L3.

An optical system of an example 2 includes in order from an object side, a planoconcave negative lens L1, a biconvex positive lens L2, and a biconvex positive lens L3.

An aperture stop S is disposed between the planoconcave negative lens L1 and the biconvex positive lens L2.

An aspheric surface is provided to a total of five surfaces which are, an image-side surface of the planoconcave negative lens L1, both surfaces of the biconvex positive lens L2, and both surfaces of the biconvex positive lens L3.

An optical system of an example 3 includes in order from an object side, a planoconcave negative lens L1, a biconvex positive lens L2, and a biconvex positive lens L3.

An aperture stop S is disposed between the planoconcave negative lens L1 and the biconvex positive lens L2.

An aspheric surface is provided to a total of five surfaces which are, an image-side surface of the planoconcave negative lens L1, both surfaces of the biconvex positive lens L2, and both surfaces of the biconvex positive lens L3.

An optical system of an example 4 includes in order from an object side, a planoconcave negative lens L1, a biconvex positive lens L2, and a biconvex positive lens L3.

An aperture stop S is disposed between the planoconcave negative lens L1 and the biconvex positive lens L2.

An aspheric surface is provided to a total of five surfaces which are, an image-side surface of the planoconcave negative lens L1, both surfaces of the biconvex positive lens L2, and both surfaces of the biconvex positive lens L3.

An optical system of an example 5 includes in order from an object side, a planoconcave negative lens L1, a biconvex positive lens L2, and a biconvex positive lens L3.

An aperture stop S is disposed between the planoconcave negative lens L1 and the biconvex positive lens L2.

An aspheric surface is provided to a total of five surfaces which are, an image-side surface of the planoconcave negative lens L1, both surfaces of the biconvex positive lens L2, and both surfaces of the biconvex positive lens L3.

An optical system of an example 6 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 7 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of six surfaces which are, both surfaces of the negative meniscus lens L1, both surfaces of the biconvex positive lens L2, and both surfaces of the biconvex positive lens L3.

An optical system of an example 8 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of six surfaces which are, both surfaces of the negative meniscus lens L1, both surfaces of the biconvex positive lens L2, and both surfaces of the biconvex positive lens L3.

An optical system of an example 9 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 10 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 11 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 12 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 13 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 14 includes in order from an object side, a biconcave negative lens L1, a biconvex positive lens L2, and a biconvex positive lens L3.

An aperture stop S is disposed between the biconcave negative lens L1 and the biconvex positive lens L2.

An aspheric surface is provided to a total of five surfaces which are, an image-side surface of the biconcave negative lens L1, both surfaces of the biconvex positive lens L2, and both surfaces of the biconvex positive lens L3.

An optical system of an example 15 includes in order from an object side, a biconcave negative lens L1, a positive meniscus lens L2 having a convex surface directed toward an image side, and a biconvex positive lens L3.

An aperture stop S is disposed between the biconcave negative lens L1 and the positive meniscus lens L2.

An aspheric surface is provided to a total of five surfaces which are, an image-side surface of the biconcave negative lens L1, both surfaces of the positive meniscus lens L2, and both surfaces of the biconvex positive lens L3.

An optical system of an example 16 includes in order from an object side, a biconcave negative lens L1, a biconvex positive lens L2, and a biconvex positive lens L3.

An aperture stop S is disposed between the biconcave negative lens L1 and the biconvex positive lens L2.

An aspheric surface is provided to a total of five surfaces which are, an image-side surface of the biconcave negative lens L1, both surfaces of the biconvex positive lens L2, and both surfaces of the biconvex positive lens L3.

An optical system of an example 17 includes in order from an object side, a biconcave negative lens L1, a biconvex positive lens L2, and a biconvex positive lens L3.

An aperture stop S is disposed between the biconcave negative lens L1 and the biconvex positive lens L2.

An aspheric surface is provided to a total of five surfaces which are, an image-side surface of the biconcave negative lens L1, both surfaces of the biconvex positive lens L2, and both surfaces of the biconvex positive lens L3.

An optical system of an example 18 includes in order from an object side, a biconcave negative lens L1, a biconvex positive lens L2, and a biconvex positive lens L3.

An aperture stop S is disposed between the biconcave negative lens L1 and the biconvex positive lens L2.

An aspheric surface is provided to a total of five surfaces which are, an image-side surface of the biconcave negative lens L1, both surfaces of the biconvex positive lens L2, and both surfaces of the biconvex positive lens L3.

An optical system of an example 19 includes in order from an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

An optical system of an example 20 includes in order form an object side, a negative meniscus lens L1 having a convex surface directed toward the object side, a biconvex positive lens L2, and a biconvex positive lens L3.

An aperture stop S is disposed between the negative meniscus lens L1 and the biconvex positive lens L2.

An aspheric surface is provided to a total of five surfaces which are, an image-side surface of the negative meniscus lens L1, both surfaces of the biconvex positive lens L2, and both surfaces of the biconvex positive lens L3.

A wide-angle optical system according to an example 21, as shown in FIG. 21, includes in order from an object side, an optical member CG, a negative meniscus lens L1 having a convex surface directed toward the object side, a biconvex positive lens L2, and a biconvex positive lens L3. The optical system including the negative meniscus lens L1, the biconvex positive lens L2, an aperture stop S, and the biconvex positive lens L3 is same as the optical system according to the example 6.

FIG. 21 is a schematic diagram illustrating that the optical member CG can be disposed. Therefore, a size and a position of the optical member CG have not been depicted accurately with respect to sizes and positions of the lenses.

The optical member CG is a member in the form of a plate, and both an object-side surface and an image-side surface thereof are curved surfaces. In FIG. 21, since both the object-side surface and the image-side surface are curved surfaces, an overall shape of the optical member CG is hemispherical. In the example 21, a thickness of the optical member CG, or in other words, a distance between the object-side surface and the image-side surface, is constant. However, the thickness of the optical member CG may not be constant.

Moreover, as it will be described later, the optical member CG is disposed at a position only 5.71 mm away on the object side from the object-side surface of the first lens. However, the optical member CG may be disposed at a position shifted frontward or rearward from the abovementioned position. Moreover, a radius of curvature and the thickness of the optical member CG mentioned here is an example, and are not limited to the radius of curvature and the thickness mentioned here.

A material that allows light to transmit through has been used for the optical member CG. Consequently, light from an object passes through the optical member CG and is incident on the negative meniscus lens L1. The optical member CG is disposed such that a curvature center of the image-side surface substantially coincides with a position of an entrance pupil. Consequently, a new aberration due to the optical member CG hardly occurs. In other words, an imaging performance of the optical system according to the example 21 is not different from an imaging performance of the optical system according to the example 6.

The optical member CG functions as a cover glass. In this case, the optical member CG corresponds to an observation window provided at an outer covering of a capsule endoscope. Therefore, the optical system according to the example 21 can be used for an optical system of a capsule endoscope. The optical systems according to the example 1 to the example 5, and the example 7 to the example 12 can also be used for an optical system of an endoscope.

Numerical data of each example described above is shown below. In Surface data, r denotes radius of curvature of each lens surface, d denotes a distance between respective lens surfaces, nd denotes a refractive index of each lens for a d-line, νd denotes an Abbe number for each lens and *denotes an aspheric surface, stop denotes an aperture stop.

In surface data of each example, a flat surface is positioned immediately next to a surface indicating a stop. This flat surface indicates an image-side surface of the stop. For example, in the example 1, a fourth surface (r4) is an object-side surface of a stop, and a fifth surface (r5) is an image-side surface of the stop. Therefore, a distance (d4) between the fourth surface and the fifth surface becomes a thickness of the stop. Similar is the case even for the other examples.

Further, in Various data, f denotes a focal length of the entire system, FNO. denotes an F number, ω denotes a half angle of view, IH denotes an image height, LTL denotes a lens total length of the optical system, BF denotes aback focus. Further, back focus is a unit which is expressed upon air conversion of a distance from a rearmost lens surface to a paraxial image surface. The lens total length is a distance from a frontmost lens surface to the rearmost lens surface plus back focus. A unit of the half angle of view is degree.

Moreover, the example 21 is an example in which the optical member CG is disposed on the object side of the image forming optical system according to the example 6. In surface data of the example 21, C1 denotes the object-side surface of the optical member CG and C2 denotes the image-side surface of the optical member CG. Since aspheric surface data and various data of the example 21 are same as aspheric surface data and various data of the example 6, description thereof is omitted here.

A shape of an aspheric surface is defined by the following expression where the direction of the optical axis is represented by z, the direction orthogonal to the optical axis is represented by y, a conical coefficient is represented by K, aspheric surface coefficients are represented by A4, A6, A8, A10, A12 . . . .

$$Z = (y^2/r)/[1+\{1-(1+k)(y/r)^2\}^{1/2}] + A4y^4 + A6y^6 + A8y^8 + A10y^{10} + A12y^{12} + \ldots$$

Further, in the aspheric surface coefficients, 'e-n' (where, n is an integral number) indicates '$10^{-n}$'. Moreover, these symbols are commonly used in the following numerical data for each example.

Example 1

| Unit mm | | | | |
|---|---|---|---|---|
| Surface data | | | | |
| Surface no. | r | d | nd | νd |
| Object plane | ∞ | 15.30 | | |
| 1 | ∞ | 0.37 | 1.53110 | 56.00 |
| 2* | 0.728 | 0.67 | | |
| 3 (Stop) | ∞ | 0.07 | | |
| 4 | ∞ | 0.04 | | |
| 5* | 24.498 | 0.95 | 1.53110 | 56.00 |
| 6* | −1.101 | 0.12 | | |
| 7* | 3.120 | 0.83 | 1.53110 | 56.00 |
| 8* | −2.065 | 1.77 | | |
| Image plane | ∞ | | | |

Aspherical surface data

2nd surface k = −1.000
A4 = 1.98427e−02, A6 = −7.55259e−03, A8 = −3.54218e−02
5th surface k = 0.000
A4 = −7.32950e−02, A6 = 1.20699e−02, A8 = −3.64246e−02
6th surface k = 0.000
A4 = −2.28259e−02, A6 = −8.36875e−04, A8 = −5.18757e−03
7th surface k = 0.000
A4 = −2.15691e−02, A6 = 3.87217e−02, A8 = −1.23224e−03
8th surface k = 0.000
A4 = 9.17782e−02, A6 = 2.34842e−02, A8 = −3.75071e−04

| Various data | |
|---|---|
| f | 1.00 |
| FNO. | 3.50 |
| 2ω | 160.7 |
| IH | 1.20 |
| LTL | 4.81 |
| BF | 1.77 |
| Φ1L | 1.10 |

Example 2

| Unit mm | | | | |
|---|---|---|---|---|
| Surface data | | | | |
| Surface no. | r | d | nd | νd |
| Object plane | ∞ | 15.02 | | |
| 1 | ∞ | 0.36 | 1.53110 | 56.00 |
| 2* | 0.710 | 0.63 | | |
| 3(Stop) | ∞ | 0.06 | | |
| 4 | ∞ | 0.04 | | |
| 5* | 103.173 | 0.94 | 1.53110 | 56.00 |
| 6* | −1.082 | 0.12 | | |
| 7* | 3.291 | 0.79 | 1.53110 | 56.00 |
| 8* | −2.041 | 1.75 | | |
| Image plane | ∞ | | | |

Aspherical surface data

2nd surface k = −0.855
A4 = 6.40408e−02, A6 = 9.80767e−03, A8 = 3.25727e−02
5th surface k = 0.000
A4 = −6.33780e−02, A6 = −4.69000e−03, A8 = 6.66947e−01
6th surface k = 0.000
A4 = −1.84952e−02, A6 = −8.07561e−03, A8 = −4.11028e−03
7th surface k = 0.000
A4 = −1.99942e−02, A6 = 5.82285e−02, A8 = −6.69696e−03
8th surface k = 0.000
A4 = 9.92888e−02, A6 = 1.50361e−02, A8 = 2.11181e−02

| Various data | |
|---|---|
| f | 1.00 |
| FNO. | 3.50 |
| 2ω | 160.6 |
| IH | 1.16 |
| LTL | 4.69 |
| BF | 1.75 |
| Φ1L | 1.05 |

Example 3

| Unit mm | | | | |
|---|---|---|---|---|
| Surface data | | | | |
| Surface no. | r | d | nd | νd |
| Object plane | ∞ | 15.70 | | |
| 1 | ∞ | 0.38 | 1.53110 | 56.00 |
| 2* | 0.751 | 0.65 | | |
| 3(Stop) | ∞ | 0.07 | | |
| 4 | ∞ | 0.06 | | |
| 5* | 8.771 | 0.93 | 1.53110 | 56.00 |
| 6* | −1.108 | 0.13 | | |
| 7* | 3.452 | 0.76 | 1.53110 | 56.00 |
| 8* | −2.123 | 1.65 | | |
| Image plane | ∞ | | | |

-continued

| Unit mm |
|---|

Aspherical surface data

2nd surface k = −1.011
A4 = −1.02760e−03, A6 = −2.63864e−02, A8 = −8.96390e−02
5th surface k = 0.000
A4 = −6.94543e−02, A6 = 1.24415e−01, A8 = −3.15019e−02
6th surface k = 0.000
A4 = −1.84612e−02, A6 = −1.26874e−03, A8 = −1.57134e−03
7th surface k = 0.000
A4 = −2.03644e−02, A6 = 3.99257e−02, A8 = −8.67688e−03
8th surface k = 0.000
A4 = 1.06729e−01, A6 = 2.53479e−02, A8 = −1.96280e−03

Various data

| | |
|---|---|
| f | 1.00 |
| FNO. | 3.50 |
| 2ω | 160.6 |
| IH | 1.22 |
| LTL | 4.63 |
| BF | 1.65 |
| Φ1L | 1.10 |

Example 4

| Unit mm |
|---|

Surface data

| Surface no. | r | d | nd | νd |
|---|---|---|---|---|
| Object plane | ∞ | 16.82 | | |
| 1 | ∞ | 0.40 | 1.53110 | 56.00 |
| 2* | 0.691 | 0.72 | | |
| 3(Stop) | ∞ | 0.07 | | |
| 4 | ∞ | 0.04 | | |
| 5* | 3.233 | 1.25 | 1.53110 | 56.00 |
| 6* | −1.186 | 0.13 | | |
| 7* | 6.734 | 0.94 | 1.53110 | 56.00 |
| 8* | −2.045 | 1.69 | | |
| Image plane | ∞ | | | |

Aspherical surface data

2nd surface k = −0.904
A4 = −2.20887e−03, A6 = −2.23635e−02, A8 = −6.10252e−04
5th surface k = 0.000
A4 = −3.67477e−02, A6 = −6.12381e−03, A8 = −7.49955e−02
6th surface k = 0.000
A4 = 7.31411e−02, A6 = −1.30999e−03, A8 = 5.26481e−05
7th surface k = 0.000
A4 = −1.72412e−03, A6 = 7.57383e−03, A8 = −2.60064e−03

-continued

| Unit mm |
|---|

8th surface k = 0.000
A4 = 3.86439e−02, A6 = 3.36045e−02, A8 = −6.74212e−04

Various data

| | |
|---|---|
| f | 1.00 |
| FNO. | 2.80 |
| 2ω | 160.6 |
| IH | 1.30 |
| LTL | 5.26 |
| BF | 1.69 |
| Φ1L | 1.21 |

Example 5

| Unit mm |
|---|

Surface data

| Surface no. | r | d | nd | νd |
|---|---|---|---|---|
| Object plane | ∞ | 16.94 | | |
| 1 | ∞ | 0.41 | 1.53110 | 56.00 |
| 2* | 0.690 | 0.69 | | |
| 3(Stop) | ∞ | 0.07 | | |
| 4 | ∞ | 0.04 | | |
| 5* | 3.267 | 1.26 | 1.53110 | 56.00 |
| 6* | −1.196 | 0.14 | | |
| 7* | 4.069 | 1.34 | 1.53110 | 56.00 |
| 8* | −2.191 | 1.47 | | |
| Image plane | ∞ | | | |

Aspherical surface data

2nd surface k = −0.833
A4 = 1.05597e−02, A6 = −3.16719e−02, A8 = −8.59068e−02
5th surface k = 0.000
A4 = 8.14672e−03, A6 = −4.89068e−02, A8 = −8.55631e−01
6th surface k = 0.000
A4 = 7.35158e−02, A6 = −1.32619e−03, A8 = −3.59462e−04
7th surface k = 0.000
A4 = −1.99401e−03, A6 = 7.36079e−03, A8 = −2.45849e−03
8th surface k = 0.000
A4 = 4.06819e−02, A6 = 3.25297e−02, A8 = −4.02299e−04

Various data

| | |
|---|---|
| f | 1.00 |
| FNO. | 2.80 |
| 2ω | 160.6 |
| IH | 1.18 |
| LTL | 5.41 |
| BF | 1.47 |
| Φ1L | 1.20 |

Example 6

Unit mm

Surface data

| Surface no. | r | d | nd | vd |
|---|---|---|---|---|
| Object plane | ∞ | 17.01 | | |
| 1 | 40.862 | 0.41 | 1.53110 | 56.00 |
| 2* | 0.688 | 0.71 | | |
| 3(Stop) | ∞ | 0.07 | | |
| 4 | ∞ | 0.04 | | |
| 5* | 3.878 | 1.26 | 1.53110 | 56.00 |
| 6* | −1.214 | 0.14 | | |
| 7* | 6.810 | 0.90 | 1.53110 | 56.00 |
| 8* | −1.902 | 1.76 | | |
| Image plane | ∞ | | | |

Aspherical surface data

2nd surface k = −0.854
A4 = 1.95794e−02, A6 = −3.13316e−02, A8 = −3.61411e−02

5th surface k = 0.000
A4 = −1.56137e−03, A6 = −2.59638e−02, A8 = −2.85807e−01

6th surface k = 0.000
A4 = 6.71372e−02, A6 = −9.48013e−04, A8 = −4.19508e−04

7th surface k = 0.000
A4 = 1.43546e−04, A6 = −5.05785e−03, A8 = −3.66190e−04

8th surface k = 0.000
A4 = 5.06637e−02, A6 = 1.35514e−02, A8 = −4.28145e−04

Various data

| | |
|---|---|
| f | 1.00 |
| FNO. | 2.80 |
| 2ω | 160.6 |
| IH | 1.30 |
| LTL | 5.29 |
| BF | 1.76 |
| Φ1L | 1.24 |

Example 7

Unit mm

Surface data

| Surface no. | r | d | nd | vd |
|---|---|---|---|---|
| Object plane | ∞ | 15.90 | | |
| 1* | 10.186 | 0.38 | 1.53110 | 56.00 |
| 2* | 0.811 | 0.61 | | |
| 3(Stop) | ∞ | 0.07 | | |
| 4 | ∞ | 0.04 | | |
| 5* | 6.128 | 1.06 | 1.53110 | 56.00 |
| 6* | −1.090 | 0.13 | | |
| 7* | 6.366 | 0.95 | 1.53110 | 56.00 |
| 8* | −1.516 | 1.43 | | |
| Image plane | ∞ | | | |

Aspherical surface data

1st surface k = −1.587
A4 = −1.83382e−04, A6 = −8.43488e−05

2nd surface k = −0.409
A4 = 1.98700e−01, A6 = −3.36079e−01, A8 = −2.47935e−02,
A10 = −7.52185e−04

5th surface k = 16.317
A4 = 9.42936e−02, A6 = 2.14734e−02, A8 = 1.82138e−02,
A10 = −8.49038e−02

6th surface k = 0.000
A4 = 1.45045e−01, A6 = −1.48681e−03, A8 = −1.24179e−03,
A10 = 2.79708e−05

7th surface k = 0.000
A4 = 5.05761e−02, A6 = −3.23424e−02, A8 = −3.13264e−04,
A10 = −2.09067e−03

8th surface k = 0.000
A4 = 8.01524e−02, A6 = 1.49181e−02, A8 = −1.72602e−04,
A10 = 9.04664e−05

Various data

| | |
|---|---|
| f | 1.00 |
| FNO. | 2.80 |
| 2ω | 160.6 |
| IH | 1.22 |
| LTL | 4.67 |
| BF | 1.43 |
| Φ1L | 1.20 |

Example 8

Unit mm

Surface data

| Surface no. | r | d | nd | vd |
|---|---|---|---|---|
| Object plane | ∞ | 14.22 | | |
| 1* | 22.773 | 0.34 | 1.53110 | 56.00 |
| 2* | 0.690 | 0.34 | | |
| 3(Stop) | ∞ | 0.06 | | |
| 4 | ∞ | 0.03 | | |
| 5* | 2.744 | 0.87 | 1.53110 | 56.00 |
| 6* | −0.948 | 0.34 | | |
| 7* | 5.693 | 0.88 | 1.53110 | 56.00 |
| 8* | −1.335 | 1.21 | | |
| Image plane | ∞ | | | |

Aspherical surface data

1st surface k = 0.000
A4 = −2.31769e−04, A6 = −9.10088e−04

2nd surface k = −0.605
A4 = 4.61074e−01, A6 = −7.29781e−01, A8 = 5.94058e−01

-continued

| Unit mm | |
|---|---|
| 5th surface | |
| k = 0.000 | |
| A4 = 2.33654e−02, A6 = −4.13962e−04, A8 = 4.00131e−01 | |
| 6th surface | |
| k = 0.000 | |
| A4 = 1.93326e−01, A6 = 6.50055e−03, A8 = 4.75639e−04 | |
| 7th surface | |
| k = 0.000 | |
| A4 = 1.11582e−01, A6 = −7.97424e−02, A8 = −1.03218e−03 | |
| 8th surface | |
| k = 0.000 | |
| A4 = 1.79893e−01 | |

| Various data | |
|---|---|
| f | 1.00 |
| FNO. | 2.80 |
| 2ω | 150.6 |
| IH | 1.15 |
| LTL | 4.09 |
| BF | 1.21 |
| Φ1L | 0.81 |

Example 9

| Unit mm | | | | |
|---|---|---|---|---|
| Surface data | | | | |
| Surface no. | r | d | nd | νd |
| Object plane | ∞ | 17.88 | | |
| 1 | 14.315 | 0.43 | 1.63500 | 23.89 |
| 2* | 0.722 | 0.70 | | |
| 3(Stop) | ∞ | 0.08 | | |
| 4 | ∞ | 0.07 | | |
| 5* | 4.325 | 1.37 | 1.53110 | 56.00 |
| 6* | −1.318 | 0.14 | | |
| 7* | 4.333 | 0.92 | 1.53110 | 56.00 |
| 8* | −2.231 | 1.92 | | |
| Image plane | ∞ | | | |

| Aspherical surface data | |
|---|---|
| 2nd surface | |
| k = −0.899 | |
| A4 = 9.77892e−04, A6 = −5.06002e−03, A8 = −6.74103e−04 | |
| 5th surface | |
| k = 0.000 | |
| A4 = 1.54212e−03, A6 = −5.97042e−03, A8 = −1.67049e−01 | |
| 6th surface | |
| k = 0.000 | |
| A4 = 2.88841e−02, A6 = −4.18197e−04, A8 = −6.11254e−04 | |
| 7th surface | |
| k = 0.000 | |
| A4 = 1.46958e−03, A6 = 3.50809e−05, A8 = 8.51036e−06 | |
| 8th surface | |
| k = 0.000 | |
| A4 = 5.14758e−02, A6 = 1.49594e−02, A8 = −9.56756e−06 | |

| Various data | |
|---|---|
| f | 1.00 |
| FNO. | 3.50 |

-continued

| Unit mm | |
|---|---|
| 2ω | 170.1 |
| IH | 1.35 |
| LTL | 5.63 |
| BF | 1.92 |
| Φ1L | 1.21 |

Example 10

| Unit mm | | | | |
|---|---|---|---|---|
| Surface data | | | | |
| Surface no. | r | d | nd | νd |
| Object plane | ∞ | 17.42 | | |
| 1 | 17.700 | 0.42 | 1.58500 | 30.00 |
| 2* | 0.720 | 0.71 | | |
| 3(Stop) | ∞ | 0.08 | | |
| 4 | ∞ | 0.07 | | |
| 5* | 4.452 | 1.29 | 1.53110 | 56.00 |
| 6* | −1.262 | 0.14 | | |
| 7* | 3.992 | 0.92 | 1.53110 | 56.00 |
| 8* | −2.313 | 1.79 | | |
| Image plane | ∞ | | | |

| Aspherical surface data | |
|---|---|
| 2nd surface | |
| k = −0.901 | |
| A4 = −2.12393e−04, A6 = −5.21650e−03, A8 = −3.35526e−03 | |
| 5th surface | |
| k = 0.000 | |
| A4 = 1.31534e−02, A6 = 1.81220e−03, A8 = −5.95567e−01 | |
| 6th surface | |
| k = 0.000 | |
| A4 = 3.47209e−02, A6 = −7.09867e−04, A8 = −7.30787e−04 | |
| 7th surface | |
| k = 0.000 | |
| A4 = 1.22046e−03, A6 = 1.77026e−03, A8 = −5.33329e−04 | |
| 8th surface | |
| k = 0.000 | |
| A4 = 5.72954e−02, A6 = 1.56246e−02, A8 = 6.88808e−04 | |

| Various data | |
|---|---|
| f | 1.00 |
| FNO. | 3.50 |
| 2ω | 164.5 |
| IH | 1.35 |
| LTL | 5.41 |
| BF | 1.79 |
| Φ1L | 1.21 |

Example 11

| Unit mm | | | | |
|---|---|---|---|---|
| Surface data | | | | |
| Surface no. | r | d | nd | νd |
| Object plane | ∞ | 16.84 | | |
| 1 | 40.062 | 0.40 | 1.53110 | 56.00 |

-continued

| Unit mm | | | | |
|---|---|---|---|---|
| 2* | 0.691 | 0.66 | | |
| 3(Stop) | ∞ | 0.07 | | |
| 4 | ∞ | 0.07 | | |
| 5* | 4.279 | 1.23 | 1.53110 | 56.00 |
| 6* | −1.219 | 0.13 | | |
| 7* | 3.929 | 0.92 | 1.53110 | 56.00 |
| 8* | −2.205 | 1.69 | | |
| Image plane | ∞ | | | |

Aspherical surface data

2nd surface k = −0.906
A4 = −2.36512e−03, A6 = −2.90489e−06, A8 = −5.42733e−06
5th surface k = 0.000
A4 = 5.31947e−03, A6 = 7.11363e−03, A8 = −7.81710e−01
6th surface k = 0.000
A4 = 3.67604e−02, A6 = −6.68120e−05, A8 = −1.38305e−03
7th surface k = 0.000
A4 = 4.54657e−03, A6 = 2.82928e−05, A8 = 2.15239e−05
8th surface k = 0.000
A4 = 6.82817e−02, A6 = 1.58918e−02, A8 = 5.42154e−04

Various data

| f | 1.00 |
|---|---|
| FNO. | 3.50 |
| 2ω | 164.5 |
| IH | 1.31 |
| LTL | 5.18 |
| BF | 1.69 |
| Φ1L | 1.15 |

Example 12

| Unit mm | | | | |
|---|---|---|---|---|
| Surface data | | | | |
| Surface no. | r | d | nd | νd |
| Object plane | ∞ | 16.73 | | |
| 1 | 30.585 | 0.40 | 1.53110 | 56.00 |
| 2* | 0.720 | 0.66 | | |
| 3 (Stop) | ∞ | 0.07 | | |
| 4 | ∞ | 0.07 | | |
| 5* | 4.602 | 1.20 | 1.53110 | 56.00 |
| 6* | −1.223 | 0.13 | | |
| 7* | 3.653 | 0.88 | 1.53110 | 56.00 |
| 8* | −2.167 | 1.65 | | |
| Image plane | ∞ | | | |

Aspherical surface data

2nd surface k = −0.900
A4 = −3.34894e−03, A6 = −9.01754e−03, A8 = −3.48473e−04
5th surface k = 0.000
A4 = 1.83069e−02, A6 = −1.54165e−02, A8 = −5.01770e−02
6th surface k = 0.000
A4 = 5.03068e−02, A6 = 1.89802e−07, A8 = 2.33732e−05
7th surface k = 0.000
A4 = 2.72172e−03, A6 = 1.72705e−04, A8 = −1.30330e−03
8th surface k = 0.000
A4 = 6.78907e−02, A6 = 1.14818e−02, A8 = −8.26989e−04

Various data

| f | 1.00 |
|---|---|
| FNO. | 3.00 |
| 2ω | 168.4 |
| IH | 1.30 |
| LTL | 5.06 |
| BF | 1.65 |
| Φ1L | 1.21 |

Example 13

| Unit mm | | | | |
|---|---|---|---|---|
| Surface data | | | | |
| Surface no. | r | d | nd | νd |
| Object plane | ∞ | 15.77 | | |
| 1 | 17.206 | 0.38 | 1.53110 | 56.00 |
| 2* | 0.705 | 0.61 | | |
| 3 (Stop) | ∞ | 0.07 | | |
| 4 | ∞ | 0.06 | | |
| 5* | 4.298 | 1.12 | 1.53110 | 56.00 |
| 6* | −1.154 | 0.13 | | |
| 7* | 3.599 | 1.00 | 1.53110 | 56.00 |
| 8* | −2.072 | 1.52 | | |
| Image plane | ∞ | | | |

Aspherical surface data

2nd surface k = −0.918
A4 = −1.32212e−02, A6 = −7.35911e−03, A8 = 7.05245e−02
5th surface k = 0.000
A4 = 2.12156e−02, A6 = −8.09560e−03, A8 = −7.00139e−01
6th surface k = 0.000
A4 = 5.90494e−02, A6 = −1.96648e−03, A8 = −9.79756e−04
7th surface k = 0.000
A4 = 3.54593e−03, A6 = 1.01067e−04, A8 = −2.90657e−03
8th surface k = 0.000
A4 = 8.06196e−02, A6 = 1.53753e−02, A8 = −7.25261e−04

Various data

| f | 1.00 |
|---|---|
| FNO. | 3.00 |
| 2ω | 140.8 |
| IH | 1.21 |
| LTL | 4.88 |
| BF | 1.52 |
| Φ1L | 1.06 |

Example 14

Unit mm

Surface data

| Surface no. | r | d | nd | νd |
|---|---|---|---|---|
| Object plane | ∞ | 16.52 | | |
| 1 | −661.199 | 0.40 | 1.53110 | 56.00 |
| 2* | 0.720 | 0.71 | | |
| 3 (Stop) | ∞ | 0.07 | | |
| 4 | ∞ | 0.04 | | |
| 5* | 3.204 | 1.20 | 1.53110 | 56.00 |
| 6* | −1.168 | 0.13 | | |
| 7* | 6.612 | 0.91 | 1.53110 | 56.00 |
| 8* | −1.990 | 1.63 | | |
| Image plane | ∞ | | | |

Aspherical surface data

2nd surface k = −0.900
A4 = 4.95085e−03, A6 = −3.54696e−03, A8 = −3.97464e−03

5th surface k = 0.000
A4 = −2.30588e−02, A6 = −1.35828e−02, A8 = −7.38038e−01

6th surface k = 0.000
A4 = 6.98964e−02, A6 = −1.16998e−03, A8 = −1.38931e−03

7th surface k = 0.000
A4 = −8.70514e−04, A6 = 5.19781e−03, A8 = 6.56479e−05

8th surface k = 0.000
A4 = 5.02615e−02, A6 = 3.26949e−02, A8 = −2.76133e−04

Various data

| | |
|---|---|
| f | 1.00 |
| FNO. | 2.80 |
| 2ω | 160.6 |
| IH | 1.28 |
| LTL | 5.09 |
| BF | 1.63 |
| Φ1L | 1.19 |

Example 15

Unit mm

Surface data

| Surface no. | r | d | nd | νd |
|---|---|---|---|---|
| Object plane | ∞ | 14.17 | | |
| 1 | −85.849 | 0.34 | 1.53110 | 56.00 |
| 2* | 0.768 | 0.54 | | |
| 3 (Stop) | ∞ | 0.06 | | |
| 4 | ∞ | 0.03 | | |
| 5* | −56.710 | 0.80 | 1.53110 | 56.00 |
| 6* | −0.936 | 0.11 | | |
| 7* | 19.492 | 0.77 | 1.53110 | 56.00 |
| 8* | −1.339 | 1.67 | | |
| Image plane | ∞ | | | |

Aspherical surface data

2nd surface k = −0.444
A4 = −6.70727e−03, A6 = −2.15827e−02, A8 = 2.22762e−02

5th surface k = 0.000
A4 = −1.59279e−01, A6 = 4.21967e−02, A8 = 2.65906e+00

6th surface k = 0.000
A4 = 1.42793e−01, A6 = −1.15662e−01, A8 = 4.15847e−04

7th surface k = 0.000
A4 = 7.26137e−02, A6 = 2.28203e−03, A8 = −9.04117e−04

8th surface k = 0.000
A4 = 7.29696e−02, A6 = 8.94791e−02, A8 = 1.12312e−02

Various data

| | |
|---|---|
| f | 1.00 |
| FNO. | 3.50 |
| 2ω | 150.8 |
| IH | 1.09 |
| LTL | 4.32 |
| BF | 1.67 |
| Φ1L | 0.92 |

Example 16

Unit mm

Surface data

| Surface no. | r | d | nd | νd |
|---|---|---|---|---|
| Object plane | ∞ | 14.21 | | |
| 1 | −24.426 | 0.34 | 1.53110 | 56.00 |
| 2* | 0.776 | 0.53 | | |
| 3 (Stop) | ∞ | 0.06 | | |
| 4 | ∞ | 0.03 | | |
| 5* | 14.175 | 0.81 | 1.53110 | 56.00 |
| 6* | −0.942 | 0.11 | | |
| 7* | 19.915 | 0.73 | 1.53110 | 56.00 |
| 8* | −1.388 | 1.63 | | |
| Image plane | ∞ | | | |

Aspherical surface data

2nd surface k = −0.399
A4 = 2.09264e−03, A6 = 5.63172e−03, A8 = −2.45116e−03

5th surface k = 0.000
A4 = −1.33871e−01, A6 = 4.50000e−02, A8 = 2.75656e−01

6th surface k = 0.000
A4 = 1.43892e−01, A6 = −1.21511e−01, A8 = −8.19243e−04

7th surface k = 0.000
A4 = 6.75870e−02, A6 = 1.56701e−02, A8 = −7.44527e−03

-continued

Unit mm

8th surface k = 0.000
A4 = 6.49817e−02, A6 = 1.10988e−01, A8 = 5.62279e−04

Various data

| | |
|---|---|
| f | 1.00 |
| FNO. | 3.50 |
| 2ω | 160.6 |
| IH | 1.09 |
| LTL | 4.25 |
| BF | 1.63 |
| Φ1L | 0.91 |

Example 17

Unit mm

Surface data

| Surface no. | r | d | nd | νd |
|---|---|---|---|---|
| Object plane | ∞ | 14.20 | | |
| 1 | −253.835 | 0.34 | 1.53110 | 56.00 |
| 2* | 0.690 | 0.31 | | |
| 3 (Stop) | ∞ | 0.06 | | |
| 4 | ∞ | 0.06 | | |
| 5* | 3.237 | 0.88 | 1.53110 | 56.00 |
| 6* | −1.030 | 0.11 | | |
| 7* | 3.107 | 0.68 | 1.53110 | 56.00 |
| 8* | −1.685 | 1.43 | | |
| Image plane | ∞ | | | |

Aspherical surface data

2nd surface k = −0.303
A4 = 3.88451e−01, A6 = −3.70357e−01, A8 = −3.97592e+00
5th surface k = 0.000
A4 = 2.47810e−01, A6 = −1.75185e−01, A8 = −2.72788e+00
6th surface k = 0.000
A4 = 5.41975e−02, A6 = −3.21763e−02, A8 = −9.95886e−03
7th surface k = 0.000
A4 = 2.17970e−02, A6 = −1.62655e−02, A8 = −1.47360e−02
8th surface k = 0.000
A4 = 1.09898e−01, A6 = 3.33263e−02, A8 = −3.23571e−03

Various data

| | |
|---|---|
| f | 1.00 |
| FNO. | 3.50 |
| 2ω | 164.4 |
| IH | 1.08 |
| LTL | 3.87 |
| BF | 1.43 |
| Φ1L | 0.75 |

Example 18

Unit mm

Surface data

| Surface no. | r | d | nd | νd |
|---|---|---|---|---|
| Object plane | ∞ | 14.44 | | |
| 1 | −11.084 | 0.35 | 1.53110 | 56.00 |
| 2* | 0.626 | 0.25 | | |
| 3 (Stop) | ∞ | 0.06 | | |
| 4 | ∞ | 0.06 | | |
| 5* | 1.967 | 0.82 | 1.53110 | 56.00 |
| 6* | −1.017 | 0.12 | | |
| 7* | 2.745 | 0.65 | 1.53110 | 56.00 |
| 8* | −1.870 | 1.40 | | |
| Image plane | ∞ | | | |

Aspherical surface data

2nd surface k = −0.826
A4 = 5.20281e−02, A6 = 1.95533e−02, A8 = 4.53709e−09
5th surface k = 0.000
A4 = 1.83732e−02, A6 = −5.82134e−01, A8 = 2.71473e−08
6th surface k = 0.000
A4 = 4.03930e−02, A6 = −5.24143e−02, A8 = −2.98486e−07
7th surface k = 0.000
A4 = 2.45840e−02, A6 = −2.60973e−02, A8 = −7.47707e−04
8th surface k = 0.000
A4 = 1.55028e−01, A6 = 6.45342e−02, A8 = −2.01409e−04

Various data

| | |
|---|---|
| f | 1.00 |
| FNO. | 3.50 |
| 2ω | 164.4 |
| IH | 1.09 |
| LTL | 3.70 |
| BF | 1.40 |
| Φ1L | 0.67 |

Example 19

Unit mm

Surface data

| Surface no. | r | d | nd | νd |
|---|---|---|---|---|
| Object plane | ∞ | 16.72 | | |
| 1 | 43.354 | 0.40 | 1.53110 | 56.00 |
| 2* | 0.666 | 0.67 | | |
| 3 (Stop) | ∞ | 0.07 | | |
| 4 | ∞ | 0.07 | | |
| 5* | 4.153 | 1.20 | 1.49236 | 57.87 |
| 6* | −1.211 | 0.13 | | |
| 7* | 3.740 | 0.78 | 1.53110 | 56.00 |
| 8* | −2.157 | 1.84 | | |
| Image plane | ∞ | | | |

-continued

| Unit mm | | | |
|---|---|---|---|
| Aspherical surface data | | | |

2nd surface k = −0.932
A4 = −1.28678e−02, A6 = 1.70338e−04, A8 = 4.79820e−04
5th surface k = 0.000
A4 = 2.87621e−02, A6 = 4.47940e−02, A8 = −6.84604e−01
6th surface k = 0.000
A4 = 3.62231e−02, A6 = 2.01230e−04, A8 = −1.15212e−03
7th surface k = 0.000
A4 = 5.45123e−03, A6 = 5.08414e−04, A8 = 3.46227e−04
8th surface k = 0.000
A4 = 6.85242e−02, A6 = 1.59451e−02, A8 = 2.78202e−04

| Various data | |
|---|---|
| f | 1.00 |
| FNO. | 3.50 |
| 2ω | 164.5 |
| IH | 1.30 |
| LTL | 5.17 |
| BF | 1.84 |
| Φ1L | 1.16 |

Example 20

| Unit mm | | | | |
|---|---|---|---|---|
| Surface data | | | | |
| Surface no. | r | d | nd | vd |
| Object plane | ∞ | 17.55 | | |
| 1 | 21.003 | 0.42 | 1.53110 | 56.00 |
| 2* | 0.710 | 0.70 | | |
| 3 (Stop) | ∞ | 0.08 | | |
| 4 | ∞ | 0.07 | | |
| 5* | 4.432 | 1.27 | 1.53110 | 56.00 |
| 6* | −1.271 | 0.14 | | |
| 7* | 4.665 | 0.89 | 1.58500 | 30.00 |
| 8* | −2.293 | 1.72 | | |
| Image plane | ∞ | | | |

| Aspherical surface data |
|---|

2nd surface k = −0.923
A4 = −8.19834e−03, A6 = −3.28514e−03, A8 = −4.23689e−05

-continued

| Unit mm |
|---|

5th surface k = 0.000
A4 = 9.79696e−03, A6 = 1.72624e−02, A8 = −8.48186e−01
6th surface k = 0.000
A4 = 3.22060e−02, A6 = 6.42515e−06, A8 = −2.41793e−03
7th surface k = 0.000
A4 = 4.48063e−03, A6 = 1.83041e−04, A8 = 2.02030e−04
8th surface k = 0.000
A4 = 6.04075e−02, A6 = 1.29127e−02, A8 = 4.25864e−04

| Various data | |
|---|---|
| f | 1.00 |
| FNO. | 3.50 |
| 2ω | 164.5 |
| IH | 1.34 |
| LTL | 5.29 |
| BF | 1.72 |
| Φ1L | 1.25 |

Example 21

| Unit mm | | | | |
|---|---|---|---|---|
| Surface data | | | | |
| Surface no. | r | d | nd | vd |
| Object plane | ∞ | 9.666 | | |
| C1 | 7.491 | 1.634 | 1.58500 | 30.00 |
| C2 | 5.857 | 5.71 | | |
| 1 | 40.862 | 0.41 | 1.53110 | 56.00 |
| 2* | 0.688 | 0.71 | | |
| 3 (Stop) | ∞ | 0.07 | | |
| 4 | ∞ | 0.04 | | |
| 5* | 3.878 | 1.26 | 1.53110 | 56.00 |
| 6* | −1.214 | 0.14 | | |
| 7* | 6.810 | 0.90 | 1.53110 | 56.00 |
| 8* | −1.902 | 1.77 | | |
| Image plane | ∞ | | | |

| Various data | |
|---|---|
| fc | 72.73 |

Next, values for conditional expressions in each example will be shown. Since an optical member CG has not been disposed in the optical systems of examples 1 to 20, values for conditional expression (14) are mentioned only in the example 21. The optical member CG in the example 21 may be used in the optical systems of examples 1 to 20.

| | Example 1 | Example 2 | Example 3 | Example 4 |
|---|---|---|---|---|
| (1) f3/f2 | 1.16 | 1.24 | 1.36 | 1.69 |
| (2) Φ1L/IH | 0.91 | 0.90 | 0.90 | 0.93 |
| (3) D1R2L/Σd | 0.25 | 0.25 | 0.26 | 0.23 |
| (4) f1/R1L | −1.12E−10 | −1.11E−10 | −1.13E−10 | −9.66E−11 |
| (5) αmax − αmin | 0.00E+00 | 0.00E+00 | 0.00E+00 | 0.00E+00 |
| (6) f1/FL | −1.37 | −1.34 | −1.42 | −1.30 |
| (7) f2/FL | 2.14 | 2.02 | 1.91 | 1.81 |
| (8) Σd/FL | 3.03 | 2.94 | 2.97 | 3.57 |
| (9) vd1/vd2 | 1.00 | 1.00 | 1.00 | 1.00 |

-continued

|  |  |  |  |  |
|---|---|---|---|---|
| (10) νd2/νd3 | 1.00 | 1.00 | 1.00 | 1.00 |
| (11) (R2L + R2R)/(R2L − R2R) | 1.09 | 0.98 | 0.78 | 0.46 |
| (12) Σd/Dmaxair | 3.93 | 4.00 | 3.79 | 4.28 |
| (13) D1Ls/FL | 1.04 | 1.00 | 1.03 | 1.12 |

|  | Example 5 | Example 6 | Example 7 | Example 8 |
|---|---|---|---|---|
| (1) f3/f2 | 1.58 | 1.52 | 1.31 | 1.47 |
| (2) Φ1L/IH | 1.02 | 0.95 | 0.98 | 1.00 |
| (3) D1R2L/Σd | 0.20 | 0.23 | 0.22 | 0.15 |
| (4) f1/R1L | −9.58E−11 | −0.032 | −0.165 | −0.059 |
| (5) αmax − αmin | 0.00E+00 | 0.00E+00 | 0.00E+00 | 0.00E+00 |
| (6) f1/FL | −1.30 | −1.32 | −1.68 | −1.35 |
| (7) f2/FL | 1.83 | 1.90 | 1.84 | 1.44 |
| (8) Σd/FL | 3.95 | 3.53 | 3.24 | 2.87 |
| (9) νd1/νd2 | 1.00 | 1.00 | 1.00 | 1.00 |
| (10) νd2/νd3 | 1.00 | 1.00 | 1.00 | 1.00 |
| (11) (R2L + R2R)/(R2L − R2R) | 0.46 | 0.52 | 0.70 | 0.49 |
| (12) Σd/Dmaxair | 4.88 | 4.27 | 4.50 | 6.57 |
| (13) D1Ls/FL | 1.10 | 1.12 | 0.99 | 0.68 |

|  | Example 9 | Example 10 | Example 11 | Example 12 |
|---|---|---|---|---|
| (1) f3/f2 | 1.40 | 1.45 | 1.45 | 1.38 |
| (2) Φ1L/IH | 0.87 | 0.89 | 0.88 | 0.93 |
| (3) D1R2L/Σd | 0.23 | 0.24 | 0.23 | 0.23 |
| (4) f1/R1L | −0.085 | −0.073 | −0.033 | −0.046 |
| (5) αmax − αmin | 6.60E−06 | 5.60E−06 | 0.00E+00 | 0.00E+00 |
| (6) f1/FL | −1.21 | −1.29 | −1.33 | −1.39 |
| (7) f2/FL | 2.08 | 2.01 | 1.94 | 1.96 |
| (8) Σd/FL | 3.71 | 3.62 | 3.49 | 3.41 |
| (9) νd1/νd2 | 0.43 | 0.54 | 1.00 | 1.00 |
| (10) νd2/νd3 | 1.00 | 1.00 | 1.00 | 1.00 |
| (11) (R2L + R2R)/(R2L − R2R) | 0.53 | 0.56 | 0.56 | 0.58 |
| (12) Σd/Dmaxair | 4.38 | 4.23 | 4.37 | 4.28 |
| (13) D1Ls/FL | 1.13 | 1.13 | 1.06 | 1.06 |

|  | Example 13 | Example 14 | Example 15 | Example 16 |
|---|---|---|---|---|
| (1) f3/f2 | 1.43 | 1.68 | 1.34 | 1.46 |
| (2) Φ1L/IH | 0.87 | 0.93 | 0.84 | 0.83 |
| (3) D1R2L/Σd | 0.22 | 0.24 | 0.24 | 0.24 |
| (4) f1/R1L | −0.081 | 0.002 | 0.017 | 0.058 |
| (5) αmax − αmin | 0.00E+00 | 0.00E+00 | 0.00E+00 | 0.00E+00 |
| (6) f1/FL | −1.39 | −1.35 | −1.43 | −1.41 |
| (7) f2/FL | 1.84 | 1.78 | 1.78 | 1.69 |
| (8) Σd/FL | 3.37 | 3.46 | 2.65 | 2.62 |
| (9) νd1/νd2 | 1.00 | 1.00 | 1.00 | 1.00 |
| (10) νd2/νd3 | 1.00 | 1.00 | 1.00 | 1.00 |
| (11) (R2L + R2R)/(R2L − R2R) | 0.58 | 0.47 | 1.03 | 0.88 |
| (12) Σd/Dmaxair | 4.53 | 4.22 | 4.17 | 4.20 |
| (13) D1Ls/FL | 0.99 | 1.11 | 0.88 | 0.87 |

|  | Example 17 | Example 18 | Example 19 | Example 20 |
|---|---|---|---|---|
| (1) f3/f2 | 1.36 | 1.58 | 1.31 | 1.37 |
| (2) Φ1L/IH | 0.70 | 0.61 | 0.89 | 0.93 |
| (3) D1R2L/Σd | 0.18 | 0.16 | 0.24 | 0.24 |
| (4) f1/R1L | 0.005 | 0.100 | −2.89E−02 | −6.63E−02 |
| (5) αmax − αmin | 0.00E+00 | 0.00E+00 | 0.00E+00 | 0.00E+00 |
| (6) f1/FL | −1.30 | −1.10 | −1.25 | −1.39 |
| (7) f2/FL | 1.58 | 1.39 | 2.06 | 2.02 |
| (8) Σd/FL | 2.43 | 2.30 | 3.33 | 3.57 |
| (9) νd1/νd2 | 1.00 | 1.00 | 0.97 | 1.00 |
| (10) νd2/νd3 | 1.00 | 1.00 | 1.03 | 1.87 |
| (11) (R2L + R2R)/(R2L − R2R) | 0.52 | 0.32 | 0.55 | 0.55 |
| (12) Σd/Dmaxair | 5.71 | 6.22 | 4.11 | 4.21 |
| (13) D1Ls/FL | 0.65 | 0.60 | 1.07 | 1.12 |

|  | Example 21 |
|---|---|
| (1) f3/f2 | 1.52 |
| (2) Φ1L/IH | 0.95 |
| (3) D1R2L/Σd | 0.23 |

-continued

| | |
|---|---|
| (4) f1/R1L | −0.032 |
| (5) αmax − αmin | 0.00E+00 |
| (6) f1/FL | −1.32 |
| (7) f2/FL | 1.90 |
| (8) Σd/FL | 3.53 |
| (9) vd1/vd2 | 1.00 |
| (10) vd2/vd3 | 1.00 |
| (11) (R2L + R2R)/(R2L − R2R) | 0.52 |
| (12) Σd/Dmaxair | 4.27 |
| (13) D1Ls/FL | 1.12 |
| (14) |Fc/FL| | 73.22 |

Figure 22:
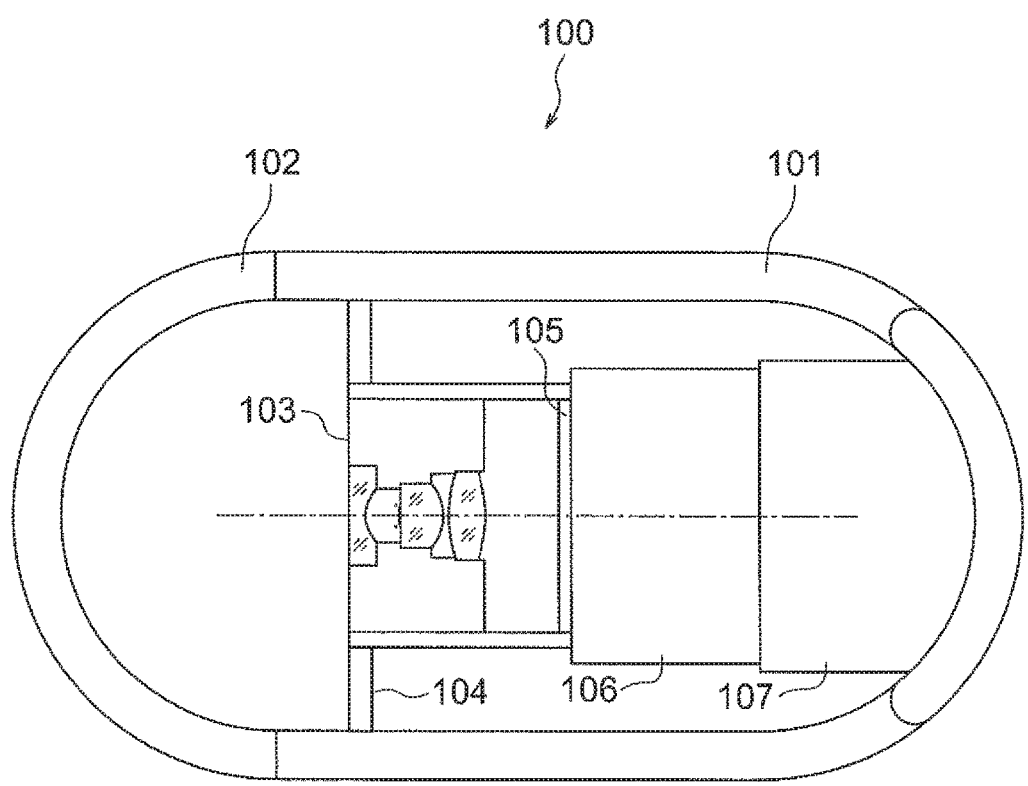
FIG. 22 is a diagrams showing a schematic arrangement of a capsule endoscope.

FIG. 22 illustrates an example of an image pickup apparatus. In this example, the image pickup apparatus is a capsule endoscope. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, an illumination unit 104, an image sensor 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image sensor 105. A drive and control of the image sensor 105 is carried out by the drive control unit 106. Moreover, an output signal from the image sensor 105 is processed by the signal processing unit 107 according to the requirement.

Here, for the image forming optical system 103, the optical system according to the abovementioned example 1 for instance, is used. In such manner, the image forming optical system 103 has a wide angle of view and an appropriate back focus, and in which an off-axis aberration is corrected favorably, while being small-sized and light-weight. Consequently, in the image forming optical system 103, a wide-angle optical image having a high resolution is acquired.

Moreover, the capsule endoscope 100 includes an optical system having a wide angle of view and an appropriate back focus, and in which an off-axis aberration is corrected favorably, while being small-sized and light-weight. Consequently, in the capsule endoscope 100, it is possible to acquire a wide-angle image with high resolution, while being small-sized and light-weight.

Figure 23A:
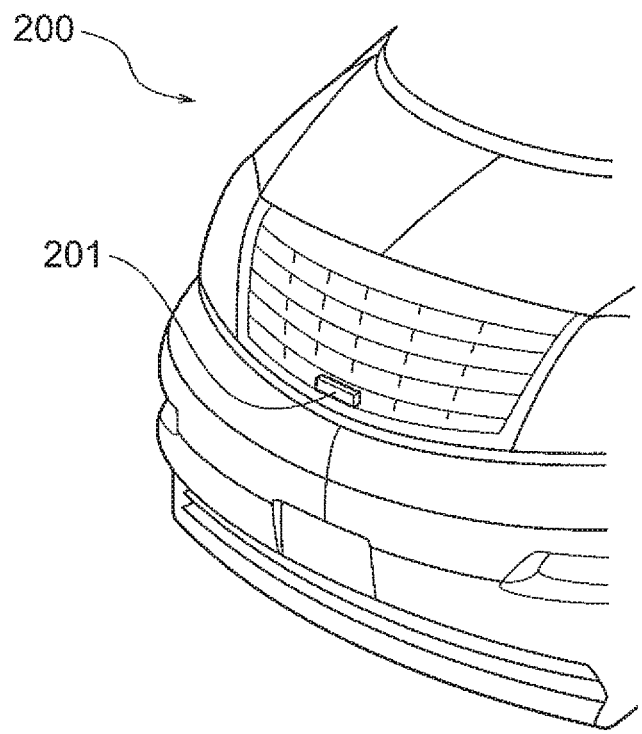
FIG. 23A and FIG. 23B are diagrams showing a car-mounted camera.
Figure 23B:
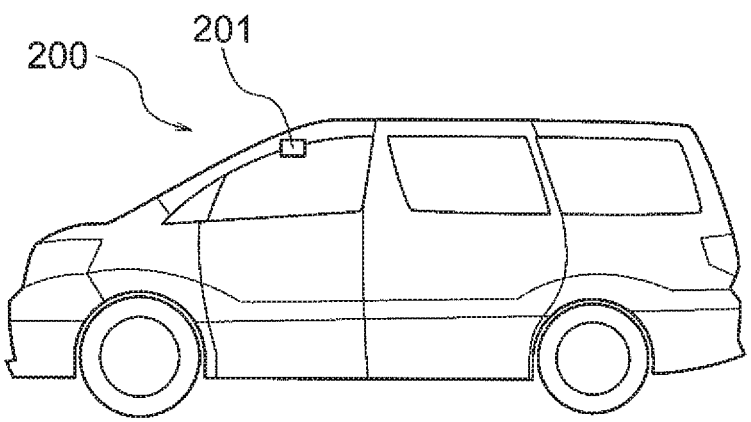

FIG. 23A and FIG. 23B are diagrams illustrating another example of an image pickup apparatus. In this example, the image pickup apparatus is a car-mounted camera. FIG. 23A is a diagram illustrating an example of a car-mounted camera mounted at an outside of a car, and FIG. 23B is a diagram illustrating an example of a car-mounted camera mounted inside a car.

As shown in FIG. 23A, a car-mounted camera 201 is provided to a front grill of an automobile 200. The car-mounted camera 201 includes an image forming optical system and an image sensor.

For the image forming optical system of the car-mounted camera 201, the optical system according to the abovementioned example 1 is used. Consequently, an optical image of an extremely wide range (the angle of view of about 160°) is formed.

As shown in FIG. 23B, the car-mounted camera 201 is provided near a ceiling of the automobile 200. An action and an effect of the car-mounted camera 201 are as have already been described. In the car-mounted camera 201, while being small-sized and light-weight, it is possible to acquire a wide-angle image with high resolution.

According to the image pickup apparatus of the present embodiment, it is possible to provide an image pickup apparatus equipped with an optical system which, while being small-sized and light-weight, has a wide angle of view and an appropriate back focus, and in which an off-axis aberration is corrected favorably. Moreover, it is possible to provide an optical apparatus which, while being small-sized and light-weight, is capable of achieving a high-resolution wide-angle optical image.

As described above, the image pickup apparatus according to the present invention is suitable for an image pickup apparatus equipped with an optical system which, while being small-sized and light-weight, has a wide angle of view and an appropriate back focus, and in which an off-axis aberration is corrected favorably. Moreover, the optical apparatus according to the present invention is suitable for an optical apparatus which, while being small-sized and light-weight, is capable of achieving a high-resolution wide-angle image.

What is claimed is:

1. An image pickup apparatus, comprising:
an optical system which includes a plurality of lenses; and
an image sensor which is disposed at an image position of the optical system, wherein
the optical system includes in order from an object side,
a first lens having a negative refractive power,
an aperture stop,
a second lens having a positive refractive power, and
a third lens having a positive refractive power, and
each of the first lens, the second lens, and the third lens is formed of a material having a refractive index not higher than 1.70, and
the following conditional expressions (1), (2), (3), (4), and (5) are satisfied:

$$0 < f3/f2 \leq 1.7 \tag{1},$$

$$0.5 < \Phi 1L/IH < 3.0 \tag{2},$$

$$0.05 < D1R2L/\Sigma d < 0.5 \tag{3},$$

$$-0.4 < f1/R1L < 0.2 \tag{4}, \text{ and}$$

$$\alpha\text{max} - \alpha\text{min} < 4.0 \times 10^{-5}/^\circ\text{C}. \tag{5},$$

where, f2 denotes a focal length of the second lens, f3 denotes a focal length of the third lens, IH denotes a maximum image height, $\Phi 1L$ denotes an effective aperture at an object-side surface of the first lens, D1R2L denotes an air space from an image-side surface of the first lens up to an object-side surface of the second lens, $\Sigma d$ denotes a distance from the object-side surface of the first lens up to a lens surface positioned nearest to image, f1 denotes a focal length of the first lens, R1L denotes a paraxial radius of curvature of the object-side surface of the first lens α max denotes a largest coefficient of linear expansion among coefficients of linear expansion at 20 degrees, of the plurality of lenses, and α min denotes a smallest coefficient of linear expansion among coefficients of linear expansion at 20, degrees of the plurality of lenses.

2. The image pickup apparatus according to claim 1, wherein the following conditional expression (6) is satisfied:

$$-3.0 < f1/FL < -0.05 \tag{6},$$

where, f1 denotes the focal length of the first lens, and

FL denotes a focal length of the overall optical system.

3. The image pickup apparatus according to claim 1, wherein the following conditional expression (7) is satisfied:

$$1.0 < f2/FL < 3.0 \tag{7},$$

where, f2 denotes the focal length of the second lens, and

FL denotes a focal length of the overall optical system.

4. The image pickup apparatus according to claim 1, wherein the following conditional expression (8) is satisfied:

$$1.0 < \Sigma d/FL < 6.0 \tag{8},$$

where, $\Sigma d$ denotes the distance from the object-side surface of the first lens up to the lens surface positioned nearest to image, and FL denotes a focal length of the overall optical system.

5. The image pickup apparatus according to claim 1, wherein the following conditional expression (9) is satisfied:

$$0.3 < vd1/vd2 < 1.2 \tag{9},$$

where, vd1 denotes Abbe number for the first lens, and vd2 denotes Abbe number for the second lens.

6. The image pickup apparatus according to claim 1, wherein the following conditional expression (10) is satisfied:

$$0.8 < vd2/vd3 < 3.0 \tag{10},$$

where, vd2 denotes Abbe number for the second lens, and vd3 denotes Abbe number for the third lens.

7. The image pickup apparatus according to claim 1, wherein the following conditional expression (11) is satisfied:

$$0.10 < (R2L+R2R)/(R2L-R2R) < 2.00 \tag{11},$$

where,

R2L denotes a paraxial radius of curvature of the object-side surface of the second lens, and R2R denotes a paraxial radius of curvature of the image-side surface of the second lens.

8. The image pickup apparatus according to claim 1, wherein the following conditional expression (12) is satisfied:

$$2.0 < \Sigma d/D\text{maxair} < 9.0 \tag{12},$$

where, $\Sigma d$ denotes the distance from the object-side surface of the first lens up to the lens surface positioned nearest to image, and Dmaxair denotes a largest air space among air spaces between the object-side surface of the first lens and the lens surface positioned nearest to image.

9. The image pickup apparatus according to claim 1, wherein the following conditional expression (13) is satisfied:

$$0.4 < D1Ls/FL < 2.0 \tag{13},$$

where,

D1Ls denotes a distance on an optical axis from the object-side surface of the first lens up to the apertures stop, and FL denotes a focal length of the overall optical system.

10. The image pickup apparatus according to claim 1, wherein a half angle of view is not less than 65 degrees.

11. The image pickup apparatus according to claim 1, comprising:

an optical member through which light passes, on the object side of the optical system, wherein both surfaces of the optical member are curved surfaces.

12. The image pickup apparatus according to claim 11, wherein the following conditional expression (14) is satisfied:

$$30 < |Fc/FL| \tag{14},$$

where,

Fc denotes a focal length of the optical member, and

FL denotes a focal length of the overall optical system.

13. An optical apparatus, comprising:

an image pickup apparatus according to claim 1; and a signal processing circuit.

* * * * *